United States Patent
Edmunds et al.

(10) Patent No.: US 9,750,246 B2
(45) Date of Patent: Sep. 5, 2017

(54) INSECTICIDAL COMPOUNDS

(71) Applicant: Syngenta Participations AG, Basel (CH)

(72) Inventors: Andrew Edmunds, Stein (CH); Andre Stoller, Stein (CH); Thomas Pitterna, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/106,489

(22) PCT Filed: Dec. 19, 2014

(86) PCT No.: PCT/EP2014/078809
§ 371 (c)(1),
(2) Date: Jun. 20, 2016

(87) PCT Pub. No.: WO2015/097091
PCT Pub. Date: Jul. 2, 2015

(65) Prior Publication Data
US 2017/0000121 A1  Jan. 5, 2017

(30) Foreign Application Priority Data
Dec. 23, 2013 (EP) .................................. 13199384

(51) Int. Cl.
| | |
|---|---|
| *C07D 213/46* | (2006.01) |
| *A01N 33/06* | (2006.01) |
| *A01N 37/34* | (2006.01) |
| *C07C 255/57* | (2006.01) |
| *C07D 213/81* | (2006.01) |
| *C07D 213/82* | (2006.01) |
| *C07D 213/89* | (2006.01) |
| *A01N 37/46* | (2006.01) |
| *A01N 43/40* | (2006.01) |
| *C07C 255/56* | (2006.01) |

(52) U.S. Cl.
CPC .............. *A01N 37/34* (2013.01); *A01N 37/46* (2013.01); *A01N 43/40* (2013.01); *C07C 255/56* (2013.01); *C07C 255/57* (2013.01); *C07D 213/81* (2013.01); *C07D 213/82* (2013.01); *C07D 213/89* (2013.01)

(58) Field of Classification Search
CPC ...... C07D 213/46; C07C 233/64; A01N 33/06
USPC ................... 564/155; 546/316; 504/101, 335
See application file for complete search history.

(56) References Cited

U.S. PATENT DOCUMENTS 8,067,638 B2 * 11/2011 Kai ...................... C07D 213/75
544/406

FOREIGN PATENT DOCUMENTS

| EP | 2394986 A1 | 12/2011 |
|---|---|---|
| JP | 2011/153115 A | 8/2011 |
| WO | 2008/075454 A1 | 6/2008 |
| WO | 2010/127928 A1 | 11/2010 |

OTHER PUBLICATIONS

International Search report and Written Opinion for PCT/EP2014/078809 dated Mar. 23, 2015.

* cited by examiner

*Primary Examiner* — Charanjit Aulakh
(74) *Attorney, Agent, or Firm* — R. Kody Jones

(57) ABSTRACT

The present invention relates to novel bisamide derivatives of formula (I) having insecticidal activity, to processes and intermediates for preparing them, to insecticidal, acaricidal, nematicidal or molluscicidal compositions comprising them and to methods of using them to combat and control insect, acarine, nematode or mollusc pests

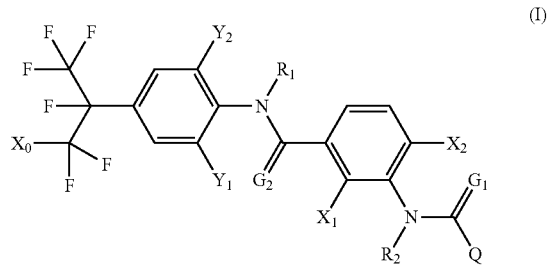

wherein $X_0$, $X_1$, $X_2$, $Y_1$, $Y_2$, $R_1$, $R_2$, $G_1$ and $G_2$, and Q are as described in formula 1 or salts and n-Oxides thereof.

7 Claims, No Drawings

INSECTICIDAL COMPOUNDS

RELATED APPLICATION INFORMATION

This application is a 371 of International Application No. PCT/EP2014/078809, filed 19 Dec. 2014, which claims priority to EP Patent Application No. 13199384.2, filed 23 Dec. 2013, the contents of which are incorporated herein by reference herein.

The present invention relates to bis-amide derivatives, to processes and intermediates for preparing them, to methods of using them to control insect, acarine, nematode and mollusc pests, and to insecticidal, acaricidal, nematicidal and molluscicidal compositions comprising them.

Compounds having insecticidal properties are known from e.g. WO2008075454, WO08075465 and WO2006137376 (=US2009233962). There exists a need for alternative methods of control of pests. Preferably, new compounds may possess improved insecticidal properties, such as improved efficacy, improved selectivity, reduced toxicity, lower tendency to generate resistance or activity against a broader range of pests. Compounds may be more advantageously formulated or provide more efficient delivery and retention at sites of action, or may be more readily biodegradable.

It has surprisingly been found that certain bisamide derivatives, which are substituted by a specific arylperfluoroalkyl group have beneficial properties, which makes them particularly suitable for use as insecticides.

The present invention therefore provides a compound of formula (I)

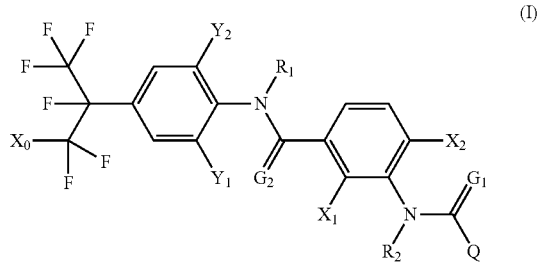

wherein
$X_0$ is bromo, chloro or hydrogen;
$X_1$ is methoxy, fluorine, or hydrogen;
$X_2$ is selected from hydrogen, cyano, methoxy, halogen, or methyl;
$Y_1$ and $Y_2$ are independently chloro, bromo, iodo, $C_1$-$C_4$alkyl, $C_1$-$C_4$haloalkyl, $C_1$-$C_4$alkoxy, and $C_1$-$C_4$haloalkoxy;
$R_1$ and $R_2$ are independent of one another hydrogen, $C_1$-$C_8$alkyl, $C_2$-$C_8$alkenyl, $C_2$-$C_8$alkynyl, $C_1$-$C_8$alkylcarbonyl, $C_1$-$C_8$alkoxycarbonyl, hydroxyl, $C_1$-$C_8$-alkyloxy, and aminocarbonyl-$C_1$-$C_4$alkylene;
$G_1$ and $G_2$ are independent of each other oxygen or sulfur;
Q represents is aryl optionally substituted by one to five $R_3$ substituents, which may be the same or different or a five membered monocyclic heterocycle containing 1 to 3 heteroatoms independently selected from nitrogen, oxygen and sulfur, optionally substituted by one to four $R_3$ substituents, which may be the same or different or a six-membered monocyclic heterocycle containing 1 to 3 heteroatoms independently selected from nitrogen, oxygen and sulfur, optionally substituted by one to five $R_3$ substituents, which may be the same or different;
$R_3$ is selected from cyano, nitro, halogen, hydroxyl, acetoxy, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkoxy-$C_1$-$C_4$alkyl, $C_1$-$C_4$alkoxy-$C_1$-$C_4$alkoxy, CN—$C_1$-$C_4$alkyl, $C_1$-$C_4$alkyl-C(O)O, $C_1$-$C_4$alkyl-S(O)$_2$, NH$_2$, $C_1$-$C_4$alkylNH, ($C_1$-$C_4$alkyl)$_2$ N, ($C_1$-$C_4$alkylO)$_2$P(O)O, phenyl and a five to six-membered monocyclic heterocycle containing 1 to 3 heteroatoms independently selected from nitrogen, oxygen and sulfur with the proviso that that (I) is not 3-benzamido-N-[4-[1-[bromo(difluoro)methyl]-1,2,2,2-tetrafluoro-ethyl]-2,6-dimethyl-phenyl]benzamide or N-[4-[1-[bromo(difluoro)methyl]-1,2,2,2-tetrafluoro-ethyl]-2-iodo-6-(trifluoromethyl)phenyl]-2-fluoro-3-[(4-fluorobenzoyl)-methyl-amino]benzamide.
or an agrochemically acceptable salt or N-Oxides thereof.

The compounds of formula (I) may exist in different geometric or optical isomers (enantiomers and/or diastereoisomers) or tautomeric forms. This invention covers all such isomers and tautomers and mixtures thereof in all proportions as well as isotopic forms such as deuterated compounds.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, isobutyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 4 carbon atoms. Alkoxy is, for example, methoxy, ethoxy, propoxy, i-propoxy, n-butoxy, isobutoxy, sec-butoxy and tert-butoxy; preferably methoxy and ethoxy.

Haloalkoxy groups preferably have a chain length of from 1 to 4 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Heterocycle in the current invention represents a five to six-membered monocyclic heterocycle containing 1 to 3 heteroatoms independently selected from nitrogen, oxygen and sulfur, and means either a 5-membered aromatic heterocyclic group or 5-membered non-aromatic heterocyclic group, or a 6-membered aromatic heterocyclic group or a 6-membered non-aromatic heterocyclic group.

"5- or 6-membered heterocyclic group, which can be substituted" in the present invention means a heterocyclic group, wherein the hydrogen atom(s) bound to the carbon atom(s), nitrogen atom(s) and/or sulphur atom(s) is/are optionally substituted by one or more atoms or groups selected from a pre-defined list, wherein the group has two or more atoms or groups selected from a pre-defined list, these atoms or groups are the same or different from each other. In context of an N atom or S atom, when it's oxidized to form an N oxide or sulphone and sulphoxide respectively, the oxidised analogue is not substituted; however, such an analogue is within the scope of the invention.

Examples of 5- or 6-membered heterocyclic group, include pyrrolidin-1-yl group, a tetrahydrofuran-2-yl group, a piperidyl group, a morpholyl group, a thiomorpholyl group, and the like.

Examples of a 5- or 6-membered aromatic heterocyclic groups, are 2-pyrroly, 2-furyl group, 3-furyl, 5-pyrazolyl, a 4-pyrazolyl, 1-pyrroly, 2-thienyl, 3-thienyl, imidazole-1-yl, a 1,2,4-triazol-1-yl, a 1,2,4-triazol-1-yl group, a 1,2,3,4-tetrazol-1-yl group, a 1,2,3,5-tetrazol-1-yl group, pyrazinyl, 4-pyrimidinyl, 5-pyrimidinyl, 2-pyridyl, 3-pyridyl, 4-pyridyl, 2-pyrimidinyl group, and the like.

The following list provides definitions, including preferred definitions, for substituents $R_1$, $R_2$, $R_3$, $X_0$, $X_1$, $X_2$, $Y_1$, $Y_2$, $G_1$, $G_2$ and Q, with reference to compounds of formula (I). For any one of these substituents, any of the definitions given below may be combined with any definition of any other substituent given below or elsewhere in this document.

Preferably $R_3$ is selected from cyano, nitro, halogen, hydroxyl, acetoxy, $C_1$-$C_4$alkyl, $C_1$-$C_4$haloalkyl, $C_1$-$C_4$alkoxy, $C_1$-$C_4$haloalkoxy, $C_1$-$C_4$alkylthio, Preferably $G^1$ and $G^2$ are both oxygen;

In a preferred embodiment of the invention, Q is a group selected from Q1, Q2, Q3, Q4 and Q5, where Q1 is a group of formula (IIa)

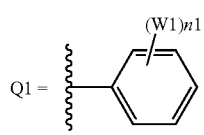

(IIa)

where the substituents W1 are independently selected from, hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy, and n1 is 0, 1 or 2

Q2 is a group of formula (IIb)

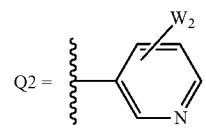

(IIb)

where $W_2$ is selected from, hydrogen, halogen, cyano, $C_1$-$C_4$ alkyl, $C_1$-$C_4$ haloalkyl, $C_1$-$C_4$ alkoxy or $C_1$-$C_4$ haloalkoxy, Q3 is a group of formula (IIc)

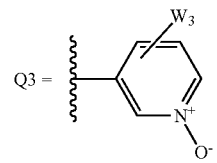

(IIc)

where $W_3$ is selected from, hydrogen, halogen, cyano, $C_1$-$C_4$ alkyl, $C_1$-$C_4$ haloalkyl, $C_1$-$C_4$ alkoxy or $C_1$-$C_4$ haloalkoxy, Q4 is a group of formula (IId)

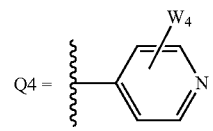

(IId)

where $W_4$ is selected, hydrogen, halogen, cyano, $C_1$-$C_4$ alkyl, $C_1$-$C_4$ haloalkyl, $C_1$-$C_4$ alkoxy or $C_1$-$C_4$ haloalkoxy, Q5 is a group of formula (IIe)

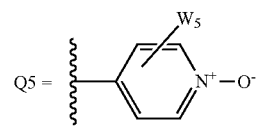

(IIe)

where $W_5$ is selected from hydrogen, halogen, cyano, $C_1$-$C_4$ alkyl, $C_1$-$C_4$ haloalkyl, $C_1$-$C_4$ alkoxy or $C_1$-$C_4$ haloalkoxy.

In a more preferred embodiment of the invention, Q is a group selected from $Q_1$, $Q_2$, $Q_3$, $Q_4$ and $Q_5$, where $Q_1$ is a group of formula (IIa)

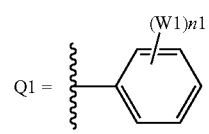

(IIa)

where the substituents $W_1$ is cyano,
and n1 is 1;
$Q_2$ is a group of formula (IIb)

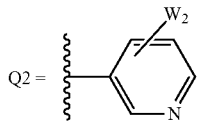

where $W_2$ is hydrogen;
$Q_3$ is a group of formula (IIc)

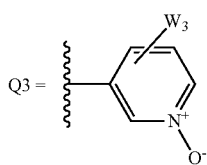

where $W_3$ is hydrogen;
Q4 is a group of formula (IId)

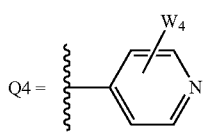

where $W_4$ is hydrogen;
and Q5 is a group of formula (IIe)

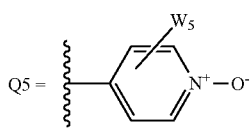

where $W_5$ is hydrogen.

In one preferred embodiment Q1 is a group of formula (IIa)
In one preferred embodiment Q2 is a group of formula (IIb)
In one preferred embodiment Q3 is a group of formula (IIc)
In one preferred embodiment Q4 is a group of formula (IId)
In one preferred embodiment Q5 is a group of formula (IIe)
In a further preferred embodiment, $Y_1$ and $Y_2$ are selected from Cl, Br, I, methyl, ethyl, methoxy, difluoromethoxy, and trifluoromethoxy,
$X_0$ is hydrogen or Br or Cl
$R_1$ is selected from hydrogen or $C_1$-$C_2$alkyl;
$R_2$ is selected from hydrogen, $C_1$-$C_2$alkyl;
$X_1$ is methoxy, fluorine or hydrogen;
$X_2$ is hydrogen;
$G^1$ and $G^2$ are both oxygen;
In an even more preferred embodiment $Y_1$ and $Y_2$ are selected from Cl, Br, ethyl, methoxy, and difluoromethoxy;
$X_0$ is Br,
$R_1$ is selected from hydrogen or $C_1$-$C_2$alkyl;
$R_2$ is selected from hydrogen, $C_1$-$C_2$alkyl;
$X_1$ is methoxy;
$X_2$ is hydrogen;
$G^1$ and $G^2$ are both oxygen;
In a further preferred embodiment $Y_1$ and $Y_2$ are selected from Cl, Br, ethyl, methoxy, and difluoromethoxy;
$X_0$ is Cl;
$R_1$ is selected from hydrogen or $C_1$-$C_2$alkyl;
$R_2$ is selected from hydrogen, $C_1$-$C_2$alkyl;
$X_1$ is methoxy;
$X_2$ is hydrogen;
$G^1$ and $G^2$ are both oxygen;
In an even more preferred embodiment $Y_1$ and $Y_2$ are selected from Cl, Br, ethyl, methoxy, and difluoromethoxy;
$X_0$ is Br,
$R_1$ is selected from hydrogen or $C_1$-$C_2$alkyl;
$R_2$ is selected from hydrogen, $C_1$-$C_2$alkyl;
$X_1$ is fluorine or hydrogen;
$X_2$ is hydrogen;
$G^1$ and $G^2$ are both oxygen;
In a further preferred embodiment $Y_1$ and $Y_2$ are selected from Cl, Br, ethyl, methoxy, and difluoromethoxy;
$X_0$ is Cl;
$R_1$ is selected from hydrogen or $C_1$-$C_2$alkyl;
$R_2$ is selected from hydrogen, $C_1$-$C_2$alkyl;
$X_1$ is fluorine or hydrogen;
$X_2$ is hydrogen;
$G^1$ and $G^2$ are both oxygen;
In a further preferred embodiment, $Y_1$ and $Y_2$ are selected from Cl, Br, I, methyl, ethyl, methoxy, difluoromethoxy, and trifluoromethoxy,
$X_0$ is hydrogen or Br or Cl
$R_1$ is selected from hydrogen or $C_1$-$C_2$alkyl;
$R_2$ is selected from hydrogen, $C_1$-$C_2$alkyl;
$X_1$ is hydrogen;
$X_2$ hydrogen, cyano, methoxy, halogen, or methyl;
$G^1$ and $G^2$ are both oxygen;
In an even more preferred embodiment $Y_1$ and $Y_2$ are selected from Cl, Br, ethyl, methoxy, and difluoromethoxy;
$X_0$ is Br,
$R_1$ is selected from hydrogen or $C_1$-$C_2$alkyl;
$R_2$ is selected from hydrogen, $C_1$-$C_2$alkyl;
$X_1$ is hydrogen;
$X_2$ cyano;
$G^1$ and $G^2$ are both oxygen;
In a further preferred embodiment $Y_1$ and $Y_2$ are selected from Cl, Br, ethyl, methoxy, and difluoromethoxy;
$X_0$ is Cl;
$R_1$ is selected from hydrogen or $C_1$-$C_2$alkyl;
$R_2$ is selected from hydrogen, $C_1$-$C_2$alkyl;
$X_1$ is hydrogen;
$X_2$ cyano;
$G^1$ and $G^2$ are both oxygen;
In an even more preferred embodiment $Y_1$ and $Y_2$ are selected from Cl, Br, ethyl, methoxy, and difluoromethoxy;
$X_0$ is Br,
$R_1$ is selected from hydrogen or $C_1$-$C_2$alkyl;
$R_2$ is selected from hydrogen, $C_1$-$C_2$alkyl;
$X_1$ is hydrogen;
$X_2$ cyano;
$G^1$ and $G^2$ are both oxygen;
In a further preferred embodiment $Y_1$ and $Y_2$ are selected from Cl, Br, ethyl, methoxy, and difluoromethoxy;
$X_0$ is Cl;
$R_1$ is selected from hydrogen or $C_1$-$C_2$alkyl;

$R_2$ is selected from hydrogen, $C_1$-$C_2$alkyl;

$X_1$ is hydrogen;

$X_2$ cyano;

$G^1$ and $G^2$ are both oxygen;

In a preferred embodiment $X_1$ is hydrogen and $X_2$ is CN;

In a further preferred embodiment $X_1$ is methoxy and $X_2$ is hydrogen;

In a further preferred embodiment of the invention $X_1$ is fluorine and $X_2$ is H;

A further aspect of the present invention relates to compounds of formula (III)

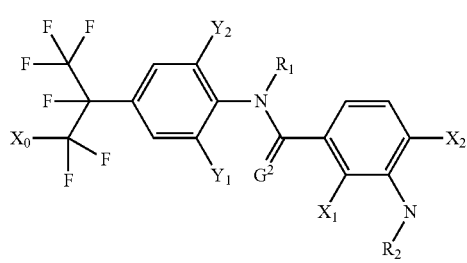

(III)

wherein $X_0$, $Y_1$, $Y_2$, $X_1$, $X_2$, $R_1$, and $R_2$ are as defined in formula (I), which are useful in the synthesis of compounds according to formula (I).

The compounds of the invention may be made by a variety of methods, for example, the methods disclosed in WO 08/000438 or WO 2010/127928.

Compounds of formula (I) may be made by treatment of compounds of formula (IV), wherein R4 is OH, $C_1$-$C_6$alkoxy, Cl, F or Br with a compound of formula III, wherein Q, $X_0$, $X_1$, $X_2$, $Y_1$, $Y_2$, $R_1$ and $R_2$ are as defined for formula I. When $R_4$ is OH, such reactions may be carried out in the presence of a coupling reagent, such as DCC (N,N'-dicyclohexylcarbodiimide), EDC (1-ethyl-3-[3-dimethyl-amino-propyl]carbodiimide hydrochloride) or BOP—Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. When $R_4$ is Cl, such reactions may be carried out under basic conditions, for example in the presence of pyridine, triethylamine, 4-(dimethylamino)pyridine or diisopropylethylamine, and optionally in the presence of a nucleophilic catalyst. Alternatively, a catalytic quantity of a iodide salt, for example potassium iodide, can be added to the acid chloride in an inert solvent, such as acetonitrile, to yield the product (see for example *Organic Letters*, 15 (3), pp. 702-705, 2013). In a further alternative, the reaction may be conducted in a biphasic system comprising an organic solvent, preferably ethyl acetate, and an aqueous solvent, preferably a solution of sodium bicarbonate. When $R_4$ is $C_1$-$C_6$alkoxy the ester may be converted directly to the amide by heating the ester and amine together in a thermal process.

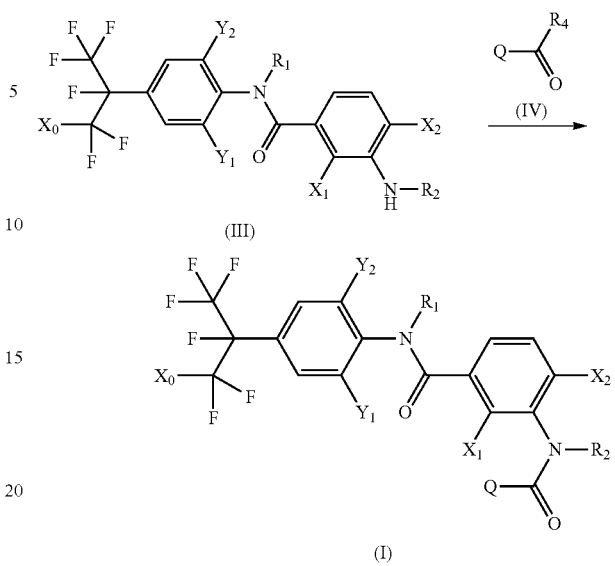

1) Compounds of formula I where in $X_0$ is hydrogen can be prepared from compounds of formula I wherein $X_0$ is Cl or Br by catalytic hydrogenation by methods known to those skilled in the art.

2) Acid halides of formula (IV), wherein $R_4$ is Cl, F or Br, may be made from carboxylic acids of formula (IV), wherein $R_4$ is OH by treatment with thionyl chloride or oxalyl chloride. 3) Carboxylic acids of formula (IV), wherein $R_4$ is OH, may be formed from esters of formula (IV), wherein $R_4$ is $C_1$-$C_6$alkoxy by treatment of the ester with an alkali hydroxide, such as sodium hydroxide, in a solvent, such as ethanol.

4) Esters of formula (IV), wherein $R_4$ is $C_1$-$C_6$alkoxy, may be made by treatment of $R_{4a}$—OH wherein $R_{4a}$ is $C_1$-$C_6$alkyl, by acylation with a carboxylic acid of formula Q-COOH or an acid halide of formula Q-COHal, wherein Hal is Cl, F or Br, under standard conditions as described in 1).

5) Compounds of formula III, can be made by formation of the N—$R_2$ bond. For example, reductive amination may be achieved by treatment of the amine IIIa with an aldehyde or ketone and a reducing agent such as sodium cyanoborohydride. Alternatively, alkylation may be achieved by treating the amine IIIa with an alkylating agent such as an alkyl halide, optionally in the presence of a base. Alternatively, arylation may be achieved by treatment of the amine with an aryl halide or sulphonate in the presence of a suitable catalyst/ligand system, often a palladium (0) complex.

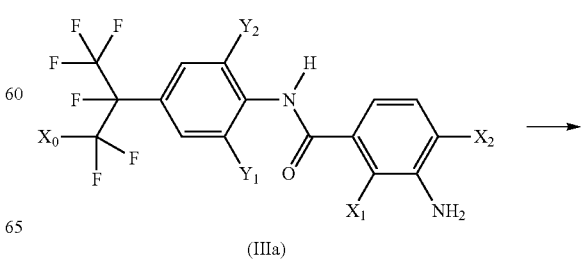

(IIIa)

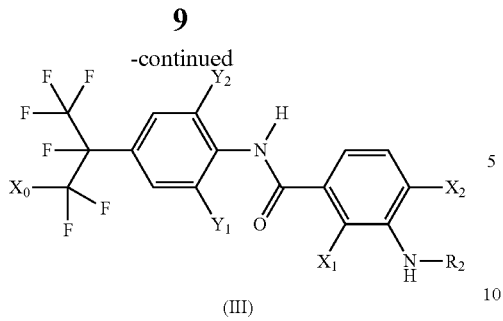

(III)

6) Compounds of formula (VI), wherein $R_5$ is $C_1$-$C_6$alkoxy, may be made from a compound of formula (V), wherein $R_5$ is $C_1$-$C_6$alkoxy and LG is a leaving group, such as bromo, chloro or sulphonate, via the displacement of the leaving group by an amine of formula $R_2$—$NH_2$ or other imine analogue followed by hydrolysis with a metal catalyst. See, for example: *Chemical Communications* 2009, (14), 1891-1893 or *Journal of Organic Chemistry*, 2000, 65(8), 2612-2614.

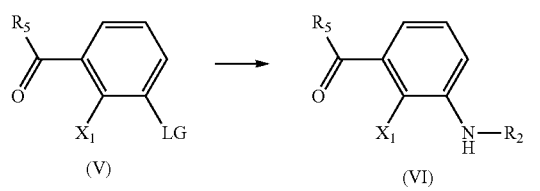

Compounds of formula (V) and amines of formula $R_2$—$NH_2$ are either known compounds or may be made by methods known to a person skilled in the art.

6a) Alternatively, compounds of formula (VI), wherein $R_5$ is C1-C6alkoxy, may be made from a compounds of formula VII, wherein $R_5$ is $C_1$-$C_6$alkoxy via reduction in the presence of a metal catalyst and a suitable two carbon building block such as acetaldehyde or acetonitrile. See for example: *J. Org. Chem.* 2007, 72, 9815 or *Org. Lett.* 2005, 7, 471

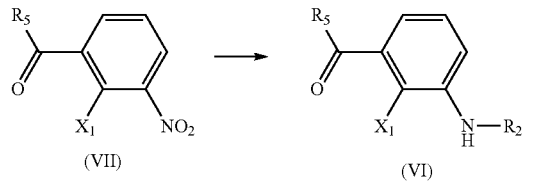

7) Alternatively, compounds of formula (I), may be made by the treatment of compounds of formula (III) with a carboxylic acid of formula Q-COOH or an acid halide of formula Q-COHal, wherein Hal is Cl, F or Br, under standard conditions as described in 1).

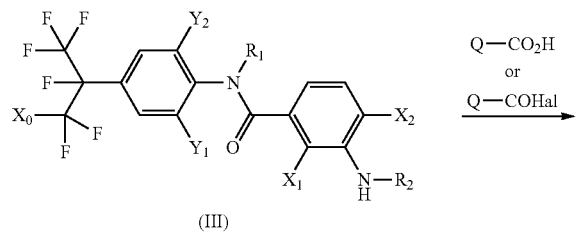

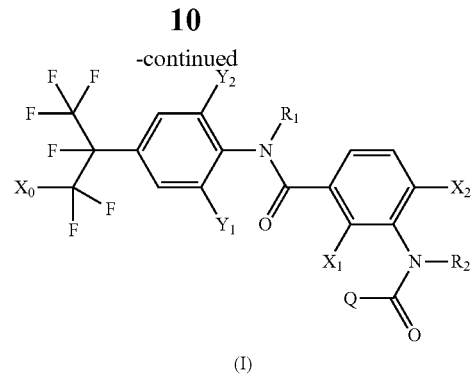

(I)

7) Compounds of formula (III) may be formed from compounds of formula (VIII), wherein P is a suitable protecting group and $R_6$ is OH, Cl or $C_1$-$C_6$alkoxy, by amide bond formation with an amine of formula (X) under standard conditions as described in 1), followed by removal of the protecting group P* under standard conditions.

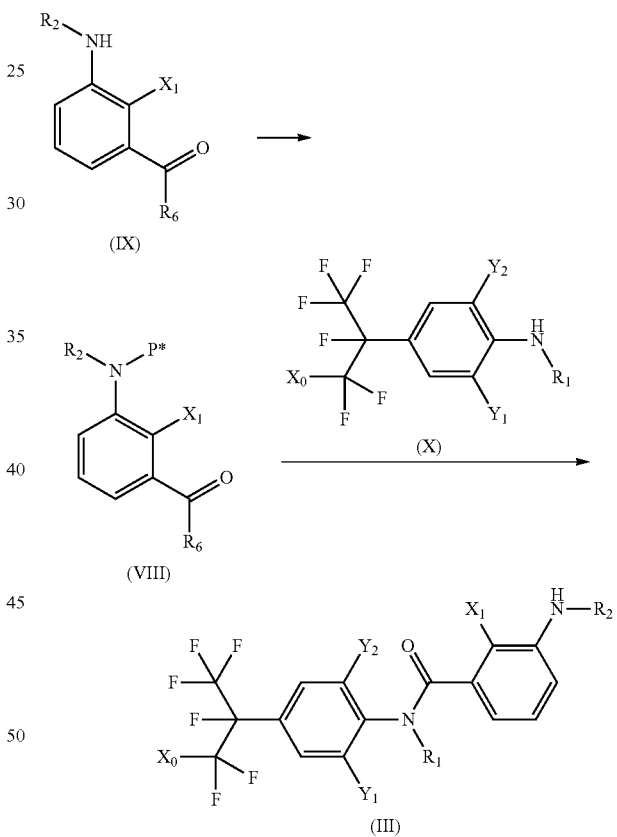

9) Compounds of formula (VIII), wherein $R_6$ is OH or $C_1$-$C_6$alkoxy, may be made by the protection of the amine functionality in compounds of formula (IX), wherein $R_6$ is OH or $C_1$-$C_6$alkoxy. Suitable protecting groups include carbamates (such as tert-butyloxycarbonyl, allyloxycarbonyl and benzyloxycarbonyl), trialkylsilyl groups (such as tert-butyldimethylsilyl) and acyl groups (such as acetyl).

10) For compounds of formula (IX) and compounds of formula (VI), the esters, wherein $R_5$ and $R_6$ is $C_1$-$C_6$alkoxy, may be hydrolysed to the acids, wherein $R_5$ and $R_6$ is OH, by treatment with an alkali hydroxide, such as sodium hydroxide, in a solvent, such as ethanol. The acids may be converted to the acid chlorides, wherein $R_5$ and $R_6$ is Cl, by treatment with thionyl chloride or oxalyl chloride as described in 2) and 3).

11) Alternatively, compounds of formula (VI), wherein $R_5$ is OH, Cl, F, Br or $C_1$-$C_6$alkoxy, may be converted directly to compounds of formula (III) by amide bond formation with an amine of formula (X) under standard conditions as described in 1).

12) Alternatively, compounds of formula (III) may be made from compounds of formula (XII), wherein LG is a leaving group such as iodo, bromo, chloro or sulphonate, by displacement of the leaving group with a compound of formula $R_2$—$NH_2$ or other imine analogue followed by hydrogenolysis with a metal catalyst. See for example: *Chemical Communications* (2009), (14), 1891-1893 or *Journal of Organic Chemistry* (2000), 65(8), 2612-2614.

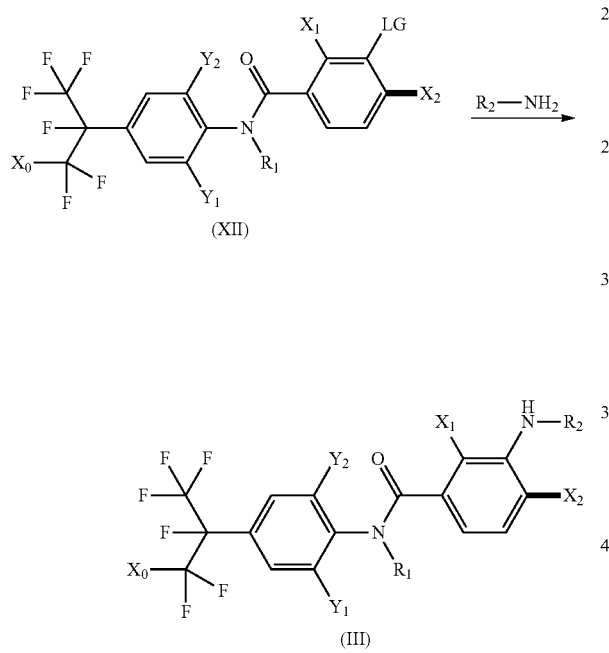

13) Compounds of formula (XII) may be made from compounds of formula (XI), wherein $R_7$ is Cl or OH and LG is a leaving group as described in 12), via amide bond formation under standard conditions as described in 1). Compounds of formula (XI) are either known compounds or may be made by methods known to the person skilled in the art.

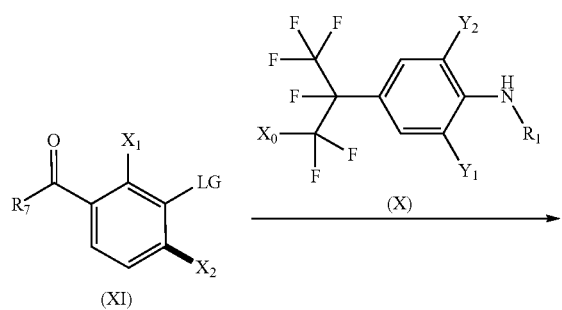

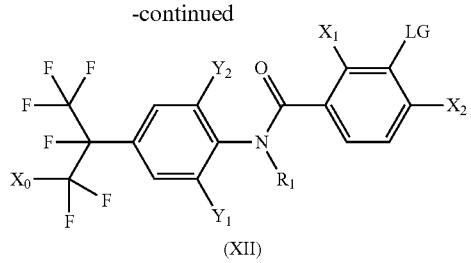

14) An alternative synthesis of compounds of formula (IIIb), wherein $R_2$ is hydrogen, may be achieved by the reduction of nitro compounds of formula (XIII), such as by treatment with tin chloride under acidic conditions, or hydrogenation catalysed by a noble metal such as palladium on carbon.

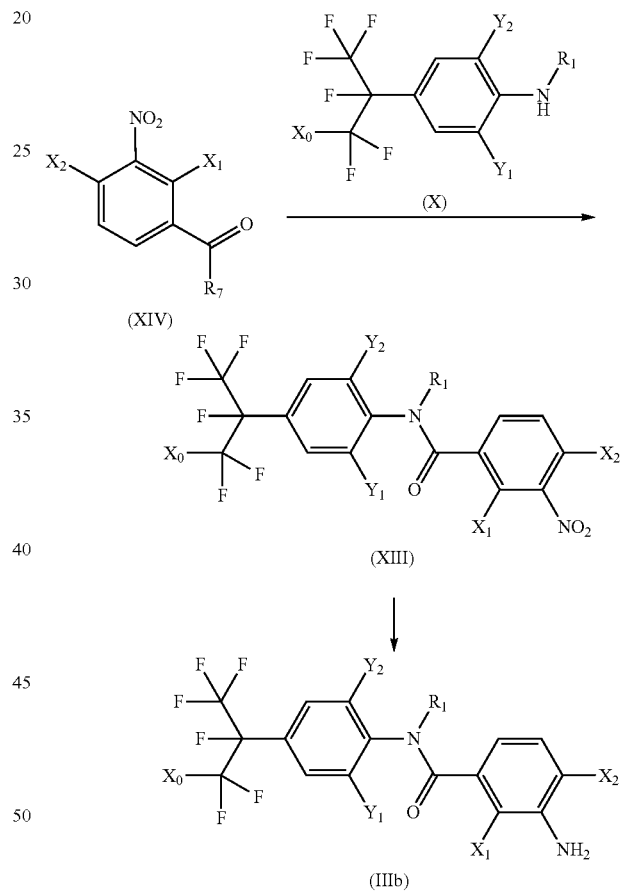

15) Compounds of formula (XIII) may be derived from compounds of formula (XIV), wherein $R_7$ is OH, Cl, or $C_1$-$C_6$alkoxy, via acylation with an amine of formula (X) under the standard conditions as described in 1).

16) For compounds of formula (XIV), the esters, wherein $R_7$ is $C_1$-$C_6$alkoxy, may be hydrolysed to the acids, wherein $R_7$ is OH, by treatment with an alkali hydroxide, such as sodium hydroxide, in a solvent, such as ethanol as described in 3). The acids may be converted to the acid chlorides, wherein $R_7$ is Cl, by treatment with thionyl chloride or oxalyl chloride as described in 2). Compounds of formula (XIV) are either known or may be made by methods known to a person skilled in the art.

17) Compounds of formula (XIV wherein $X_1$ is F (XIVa) can be made from a compound of formula (XV) wherein LG is a leaving group, such as diazonio or chlorine, by reaction with fluoride, such as KF.

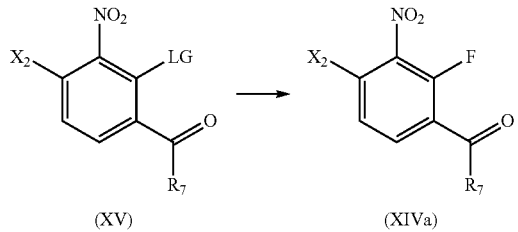

The displacement of a halogen with a fluoride nucleophile can also be carried out on intermediates of formula (XIII) in the cases where $X_1$ is LG as defined in compounds of formula (XV).

18) Compounds of formula (XIII) where $R_1$ is selected from $C_1$-$C_8$alkyl, $C_2$-$C_8$alkenyl, $C_2$-$C_8$alkynyl, may be prepared from compounds of formula (XIII) where $R_1$ is hydrogen, by treating them with a base, followed by an appropriate electrophile. Example of bases can be metal hydrides, like sodium hydride, potassium hydride or calcium hydride or metal alkoxide, like potassium t-butoxide, or organometals, like methyllithium, butyllithium, alkylmagnesium halide, metal amides like lithium diisopropylamide or lithium hexamethyldisilazide or a basic salt, like potassium carbonate. A solvent can be used. It could be, for example, a polar aprotic solvent like DMF or an ether like THF or dimethoxyethane. The reaction can be performed below 0° C. or above 80° C., but preferably in DMF between 0° C. and 25° C. The electrophile is $R^2$—X' where $R^2$ is selected from $C_1$-$C_8$alkyl, $C_2$-$C_8$alkenyl, $C_2$-$C_8$alkynyl and X' is a leaving group like bromide, chloride, iodide, mesylate, triflate, tosylate and the like. The base can be used in excess, as well as the electrophile, but preferably, the base is used in equivalent amounts as well as the electrophilic reagent.

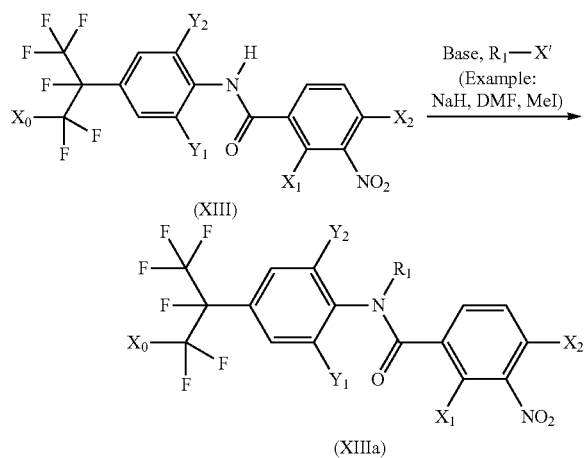

19) Compounds of formula (I) wherein Q is as defined in the description, $R^2$ is different from hydrogen and $R^1$ is selected from $C_1$-$C_8$alkyl, $C_2$-$C_8$alkenyl, $C_2$-$C_8$alkynyl, may be prepared from compound of formula (Ia) wherein Q is as defined in the description, $R_2$ is different from hydrogen and $R_1$ is hydrogen, by treating it with a base, followed by an appropriate electrophile. Example of bases can be metal hydrides, like sodium hydride, potassium hydride or calcium hydride or metal alkoxide, like potassium t-butoxide, or organometals, like methyllithium, butyllithium, alkylmagnesium halide, metal amides like lithium diisopropylamide or lithium hexamethyldisilazide or a basic salt, like potassium carbonate. A solvent can be used. It could be, for example, a polar aprotic solvent like DMF or an ether like THF or dimethoxyethane. The reaction can be performed below 0° C. or above 80° C., but preferably in DMF between 0° C. and 25° C. The electrophile is $R_1$—X' where $R_1$ is selected from $C_1$-$C_8$alkyl, $C_2$-$C_8$alkenyl, $C_2$-$C_8$alkynyl and X' is a leaving group like bromide, chloride, iodide, mesylate, triflate, tosylate and the like. The base can be used in excess, as well as the electrophile, but preferably, the base is used in equivalent amounts as well as the electrophilic reagent. Preferred conditions are sodium hydride in DMF between 0° C. and 25° C.

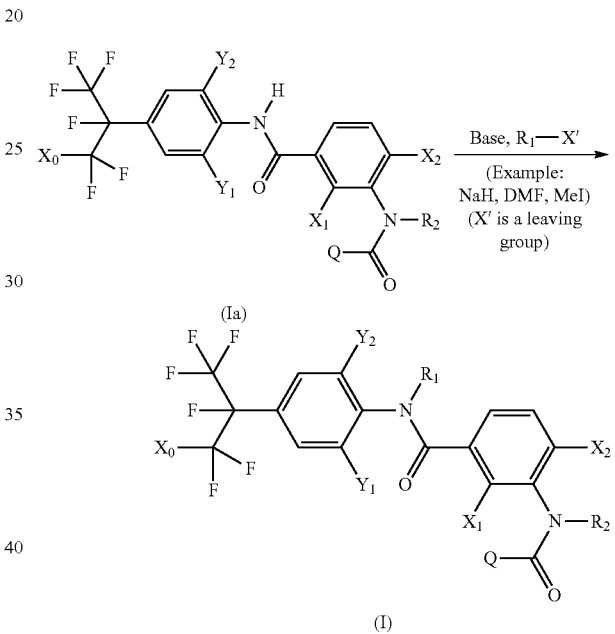

20) Compounds of formula (I) wherein Q is as defined in the description, $R_2$ is selected from $C_1$-$C_8$alkyl, $C_2$-$C_8$alkenyl, $C_2$-$C_8$alkynyl and $R_1$ is different from hydrogen, may be prepared from compound of formula (Ic) wherein Q is as defined in the description, $R_2$ is hydrogen and $R_1$ is different from hydrogen, by treating it with a base, followed by an appropriate electrophile. Example of bases can be metal hydrides, like sodium hydride, potassium hydride or calcium hydride or metal alkoxide, like potassium t-butoxide, or organometals, like methyllithium, butyllithium, alkylmagnesium halide, metal amides like lithium diisopropylamide or lithium hexamethyldisilazide or a basic salt, like potassium carbonate. A solvent can be used. It could be, for example, a polar aprotic solvent like DMF or an ether like THF or dimethoxyethane. The reaction can be performed below 0° C. or above 80° C., but preferably in DMF between 0° C. and 25° C. The electrophile is $R_2$—X' where $R_2$ is selected from $C_1$-$C_8$alkyl, $C_2$-$C_8$alkenyl, $C_2$-$C_8$alkynyl and X' is a leaving group like bromide, chloride, iodide, mesylate, triflate, tosylate and the like. The base can be used in excess, as well as the electrophile, but preferably, the base is used in equivalent amounts as well as the electrophilic reagent. Preferred conditions are sodium hydride in DMF between 0° C. and 25° C.

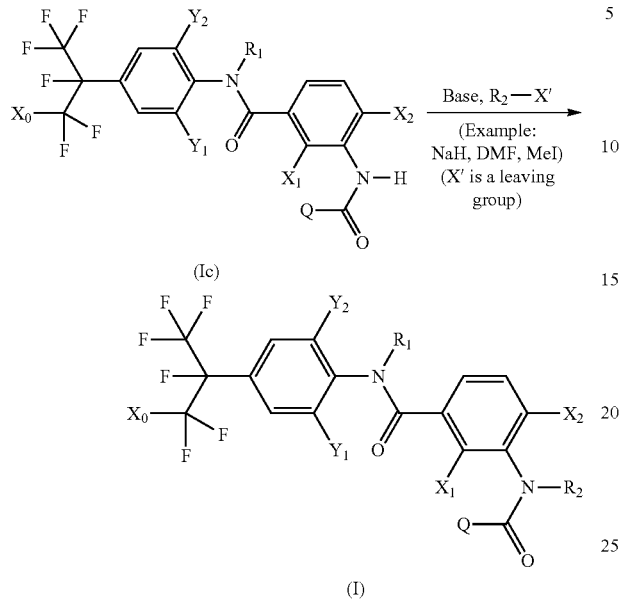

Compounds of formula I wherein $Y_1$, $Y_2$, $R_1$, $G_1$, $X_1$, $X_2$, $R_2$, $G_2$ and Q are as described in formula I, and $X_0$ is hydrogen (i.e. compounds of formula Id), can be obtained from compounds of formula I where $X_0$ is chlorine or bromine by reduction, for example with a tris-(trimethylsilyl)silane, in an inert solvent at temperatures between 30-150° C., in the presence of a radical initiator such as Azo-bis-(isobutyronitril), or alternatively with a metal such as iron, in an acidic medium (Bechamp reduction).

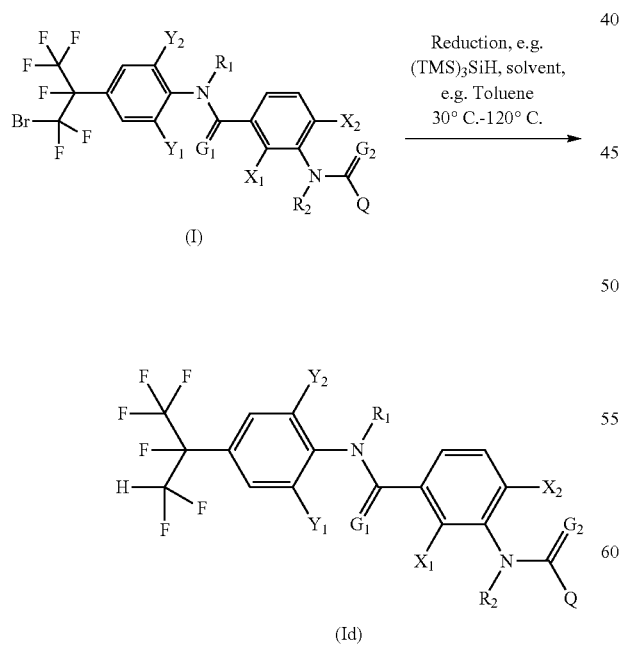

Compounds of formula (X) can be prepared according to the following scheme:

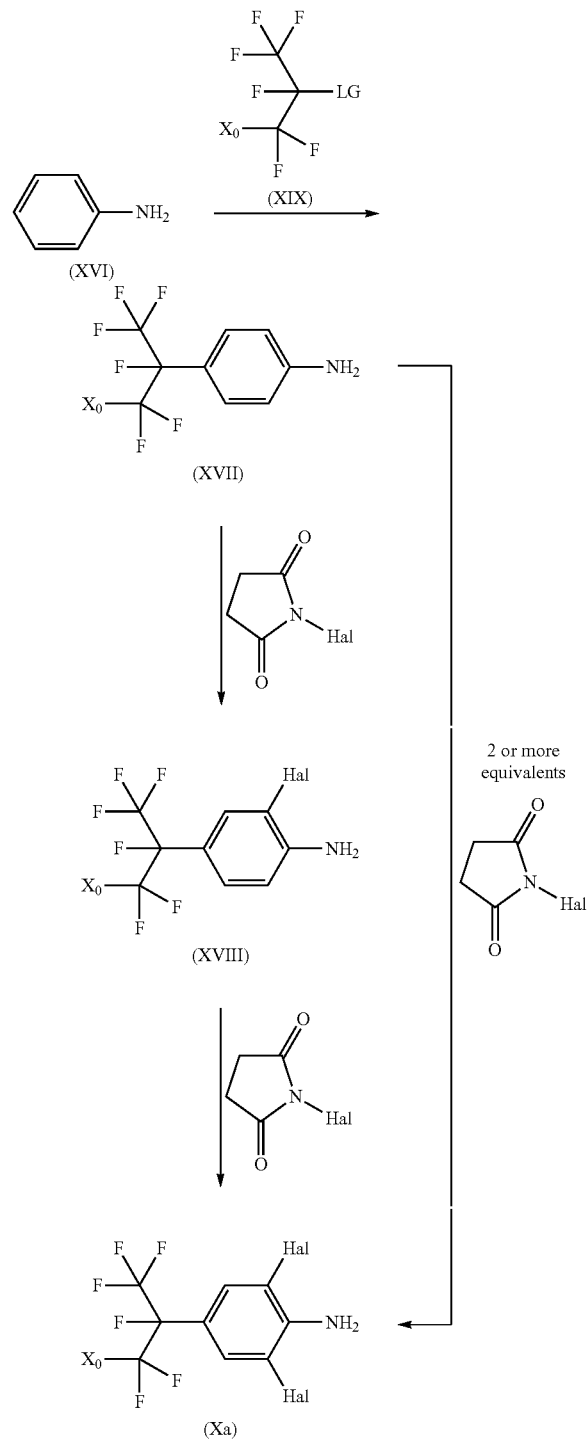

In the scheme above, aniline (XVI) is treated with a compound of formula (XIX) (wherein when $X_0$ is bromo, LG is bromine and when $X_0$ is chlorine, LG is Iodo) in an inert solvent mixture, such as tert-butyl methyl ether and water, in the presence of sodium dithionite at ambient temperature, in the presence of a phase transfer catalyst (for example tetrabutylammonium hydrogen sulphate) to give compounds of formula XVII. Compounds of formula XVII can be converted to compounds of formula (Xa), wherein Hal is Cl, Br, or I, by treatment with 2 or more equivalents of N-halosuccinamide in a polar aprotic solvent such as dimethyl formamide, or N-methyl pyrollidine at temperatures. The compounds of formula (Xa) so obtained have the same halogens (chloro, bromo or iodo) at the 2,6-positions of the aniline (Xa). Alternatively, the halogens can be introduced sequentially by treatment 1 equivalent of N-halosucciniamide, to give an intermediate of formula (XVIII), which upon treatment with a further equivalent of N-halosucciniamide leads to compounds of formula (Xa) wherein the halogens at the 2,6 positions of (Xa) are different from each other. Alternatively, compounds of formula X can be prepared as shown in the following scheme

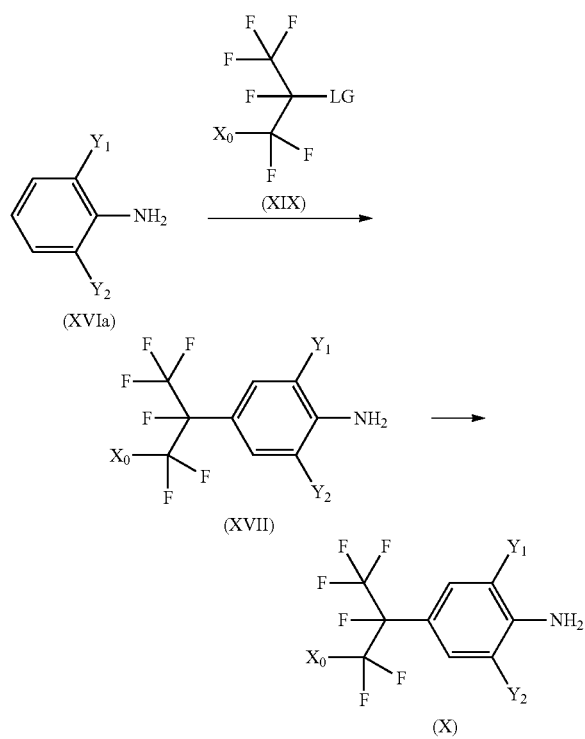

In the above scheme, treatment of compounds of formula (XVIa) wherein $Y_1$ is $C_1$-$C_4$alkyl, $C_1$-$C_4$haloalkyl, $C_1$-$C_4$alkoxy, or $C_1$-$C_4$haloalkoxy and $Y_2$ is hydrogen or $C_1$-$C_4$alkyl upon treatment with compounds of formula XIX as described above leads to compounds of formula XVIIa wherein $Y_1$ is $C_1$-$C_4$alkyl, $C_1$-$C_4$haloalkyl, $C_1$-$C_4$alkoxy, or $C_1$-$C_4$haloalkoxy and $Y_2$ is hydrogen or $C_1$-$C_4$alkyl. Compounds of formula (XVIIa) wherein $Y_2$ is hydrogen upon treatment with N-halosuccinamide as described previously leads to compounds of formula X wherein $Y_1$ is $C_1$-$C_4$alkyl, $C_1$-$C_4$haloalkyl, $C_1$-$C_4$alkoxy, or $C_1$-$C_4$haloalkoxy and $Y_2$ is Cl, Br, or I. Compounds of formula (XIX) can be prepared according to literature procedures (see Eur. Pat. Appl., 1418163 when LG and $X_0$ are Br, and *J. Amer. Chem. Soc.* 83, 2495-500, 1961, when LG is I and $X_0$ is Cl)

The compounds according to the invention, namely the compounds of formula (I) and (III), and the compounds mentioned in the method according to the invention may exist in different geometric or optical isomers or tautomeric forms.

This invention covers all such isomers and tautomers and mixtures thereof in all proportions as well as isotopic forms such as deuterated compounds.

The invention also covers salts of all compounds of the invention.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of the abovementioned animal pests are:
from the order Acarina, for example,
*Acalitus* spp., *Aculus* spp., *Acaricalus* spp., *Aceria* spp., *Acarus siro*, *Amblyomma* spp., *Argas* spp., *Boophilus* spp., *Brevipalpus* spp., *Bryobia* spp., *Calipitrimerus* spp., *Chorioptes* spp., *Dermanyssus gallinae*, *Dermatophagoides* spp., *Eotetranychus* spp., *Eriophyes* spp., *Hemitarsonemus* spp., *Hyalomma* spp., *Ixodes* spp., *Olygonychus* spp., *Ornithodoros* spp., *Polyphagotarsone latus*, *Panonychus* spp., *Phyllocoptruta oleivora*, *Phytonemus* spp., *Polyphagotarsonemus* spp., *Psoroptes* spp., *Rhipicephalus* spp., *Rhizoglyphus* spp., *Sarcoptes* spp., *Steneotarsonemus* spp., *Tarsonemus* spp., and *Tetranychus* spp.;
from the order Anoplura, for example,
*Haematopinus* spp., *Linognathus* spp., *Pediculus* spp., *Pemphigus* spp., and *Phylloxera* spp.;
from the order Coleoptera, for example,
*Agriotes* spp., *Amphimallon majale*, *Anomala orientalis*, *Anthonomus* spp., *Aphodius* spp., *Astylus atromaculatus*, *Ataenius* spp., *Atomaria linearis*, *Chaetocnema tibialis*, *Cerotoma* spp., *Conoderus* spp., *Cosmopolites* spp., *Cotinis nitida*, *Curculio* spp., *Cyclocephala* spp., *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp., *Maecolaspis* spp., *Maladera castanea*, *Megascelis* spp., *Melighetes aeneus*, *Melolontha* spp., *Myochrous armatus*, *Orycaephilus* spp., *Otiorhynchus* spp., *Phyllophaga* spp., *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp., *Sphenophorus* spp., *Sternechus subsignatus*, *Tenebrio* spp., *Tribolium* spp., and *Trogoderma* spp.;
from the order Diptera, for example,
*Aedes* spp., *Anopheles* spp., *Antherigona soccata*, *Bactrocea oleae*, *Bibio hortulanus*, *Bradysia* spp., *Calliphora erythrocephala*, *Ceratitis* spp., *Chrysomyia* spp., *Culex* spp., *Cuterebra* spp., *Dacus* spp., *Delia* spp., *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp., *Rivelia quadrifasciata*, *Scatella* spp., *Sciara* spp., *Stomoxys* spp., *Tabanus* spp., *Tannia* spp., and *Tipula* spp.;
from the order Hemiptera, for example,
*Acanthocoris scabrator*, *Acrosternum* spp., *Adelphocoris lineolatus*, *Amblypelta nitida*, *Bathycoelia thalassina*, *Blissus* spp., *Cimex* spp., *Clavigralla tomentosicollis*, *Creontia-* des spp., *Distantiella theobroma*, *Dichelops furcatus*, *Dysdercus* spp., *Edessa* spp., *Euchistus* spp., *Eurydema pulchrum*, *Eurygaster* spp., *Halyomorpha halys*, *Horcias nobilellus*, *Lep-tocorisa* spp., *Lygus* spp., *Margarodes* spp., *Murgantia histrionic*, *Neomegalotomus* spp., *Nesidiocoris tenuis*, *Nezara* spp., *Nysius simulans*, *Oebalus insularis*, *Piesma* spp., *Piezodorus* spp., *Rhodnius* spp., *Sahlbergella singularis*, *Scaptocoris castanea*, *Scotinophara* spp., *Thyanta* spp., *Triatoma* spp., *Vatiga illudens*;

*Acyrthosium pisum*, *Adalges* spp., *Agalliana ensigera*, *Agonoscena targionii*, *Aleurodicus* spp., *Aleurocanthus* spp., *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp., *Brachycaudus* spp., *Brevicoryne brassicae*, *Cacopsylla* spp., *Cavariella aegopodii* Scop., *Ceroplaster* spp., *Chrysomphalus aonidium*, *Chrysomphalus dictyospermi*, *Cicadella* spp., *Cofana spectra*, *Cryptomyzus* spp., *Cicadulina* spp., *Coccus hesperidum*, *Dalbulus maidis*, *Dialeurodes* spp., *Diaphorina citri*, *Diuraphis noxia*, *Dysaphis* spp., *Empoasca* spp., *Eriosoma larigerum*, *Erythroneura* spp., *Gascardia* spp., *Glycaspis brimblecombei*, *Hyadaphis pseudobrassicae*, *Hyalopterus* spp., *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp., *Metcalfa pruinosa*, *Metopolophium dirhodum*, *Myndus crudus*, *Myzus* spp., *Neotoxoptera* spp., *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp., *Phorodon humuli*, *Phylloxera* spp., *Planococcus* spp., *Pseudaulacaspis*, *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatellafurcifera*, *Spissistilusfestinus*, *Tarophagus Proserpina*, *Toxoptera* spp., *Trialeurodes* spp., *Tridiscus sporoboli*, *Trionymus* spp., *Trioza erytreae*, *Unaspis citri*, *Zyginaflammigera*, *Zyginidia scutellaris*;

from the order Hymenoptera, for example,

*Acromyrmex*, *Arge* spp., *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp., *Slenopsis invicta*, *Solenopsis* spp., and *Vespa* spp.;

from the order Isoptera, for example,

*Coptotermes* spp., *Corniternes cumulans*, *Incisitermes* spp., *Macrotermes* spp., *Mastotermes* spp., *Microtermes* spp., *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp., *Argyrotaenia* spp., *Autographa* spp., *Bucculatrix thurberiella*, *Busseolafusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophilaflava*, *Crambus* spp., *Crocidolomia binotalis*, *Cryptophlebia leucotreta*, *Cydalimaperspectalis*, *Cydia* spp., *Diaphania perspectalis*, *Diatraea* spp., *Diparopsis castanea*, *Earias* spp., *Eldana saccharina*, *Ephestia* spp., *Epinotia* spp., *Estigmene acrea*, *Etiella zinckinella*, *Eucosma* spp., *Eupoecilia ambiguella*, *Euproctis* spp., *Euxoa* spp., *Feltiajaculiferia*, *Grapholita* spp., *Hedya nubiferana*, *Heliothis* spp., *Hellula undalis*, *Herpetogramma* spp., *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp., *Noctua* spp., *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp., *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp., and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp., and *Schistocerca* spp.;

from the order Psocoptera, for example,

*Liposcelis* spp.;

from the order Siphonaptera, for example,

*Ceratophyllus* spp., *Ctenocephalides* spp., and *Xenopsylla cheopis*;

from the order Thysanoptera, for example,

*Calliothrips phaseoli*, *Frankliniella* spp., *Heliothrips* spp., *Hercinothrips* spp., *Parthenothrips* spp., *Scirtothrips aurantii*, *Sericothrips variabilis*, *Taeniothrips* spp., *Thrips* spp.;

from the order Thysanura, for example,

*Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

As for acari, for example, *Tetranychus cinnabarinus, Tetranychus urticae, Panonychus citri, Aculops pelekassi, Tarsonemus* spp.

As for nematodes, for example, *Meloidogyne incognita, Bursaphelenchus lignicolus Mamiya et Kiyohara, Aphelenchoides besseyi, Heterodera glycines, Pratylenchus* spp.

Additionally, the compounds can be used for controlling animal pests, in particular insects, arachnids, helminths, nematodes and molluscs, which are encountered in agriculture, in horticulture, the field of veterinary medicine, in forests, in gardens and leisure facilities, in the protection of stored products and of materials, and in the hygiene sector. They may preferably be employed as plant protection agents. They may be active against normally sensitive and resistant species and against all or some stages of development.

These pests include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetoniajucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*.

It may be furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossusphyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphonfragaefolii, Chionaspis tegalensis, Chlorita onukii, Chromaphis juglandicola, Chrysomphalusficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarvafimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Plano-* coccus spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatellafurcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Mono-morium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneurafumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

Furthermore, in the field of veterinary medicine, the novel compounds of the present invention can be effectively used against various harmful animal parasitic pests (endoparasites and ectoparasites), for example, insects and helminthes.

Examples of such animal parasitic pests include the pests as described below.

Examples of the insects include *Gasterophilus* spp., *Stomoxys* spp., *Trichodectes* spp., *Rhodnius* spp., *Ctenocephalides canis*, *Cimx lecturius*, *Ctenocephalides felis*, *Lucilia cuprina*, and the like.

Examples of acari include *Ornithodoros* spp., *Ixodes* spp., *Boophilus* spp., and the like.

In the veterinary fields, e.g. in the field of veterinary medicine, the active compounds according to the present invention are active against animal parasites, in particular ectoparasites or endoparasites.

The term endoparasites includes in particular helminths, such as cestodes, nematodes or trematodes, and protozoae, such as coccidia.

Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus*; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gastero-

*philus intestinalis, Gasterophilus haemorroidalis, Gasterophilus inermis, Gasterophilus nasalis, Gasterophilus nigricornis, Gasterophilus pecorum, Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*; from the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp., (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp., (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentorpictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals.

Animals include agricultural livestock such as, for example, cattle, sheep, goats, horses, pigs, donkeys, camels, buffaloes, rabbits, chickens, turkeys, ducks, geese, cultured fish, honeybees.

Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it may be desirable to prevent or interrupt the uptake of blood by the parasites from the hosts.

Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels.

More specifically, "controlling", as used herein, means that the active compound is effective in killing the respective parasite, inhibiting its growth, or inhibiting its proliferation. Generally, when used for the treatment of animals the active compounds according to the invention can be applied directly.

Preferably they are applied as pharmaceutical compositions which may contain pharmaceutically acceptable excipients and/or auxiliaries which are known in the art.

In the veterinary field and in animal keeping, the active compounds are applied (e.g. administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80 percent by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

In the present invention, a substance having an insecticidal action against pests including all of these is referred to as an insecticide.

An active compound of the present invention can be prepared in conventional formulation forms, when used as an insecticide.

Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like.

These formulations can be produced by methods that are known per se.

For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like. The liquefied gas diluent or carrier may be those which are gaseous at normal temperature and normal pressure, for example, aerosol propellants such as butane, propane, nitrogen gas, carbon dioxide and halogenated hydrocarbons. Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like. Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like. Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydro lyzate, and the like. Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like. Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc. The formulations in general can contain the active ingredient in an amount ranging from 0.1 to 95 percent by weight, and preferably 0.5 to 90 percent>by weight. The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100 percent by weight, and preferably 0.00001 to 1 percent by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents.

Further embodiments of the invention are described below.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips*, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs Examples of pest species which may be controlled by the compounds of formula (I) include: *Myzus persicae* (aphid), *Aphis gossypii* (aphid), *Aphis fabae* (aphid), *Lygus* spp., (capsids), *Dysdercus* spp., (capsids), *Nilaparvata lugens* (planthopper), *Nephotettixc incticeps* (leafhopper), *Nezara* spp., (stinkbugs), *Euschistus* spp., (stinkbugs), *Leptocorisa* spp., (stinkbugs), *Frankliniella occidentalis* (thrip), *Thrips* spp., (*thrips*), *Leptinotarsa decemlineata* (Colorado potato beetle), *Anthonomus grandis* (boll weevil), *Aonidiella* spp., (scale insects), *Trialeurodes* spp., (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp., (cutworms), *Chilo suppressalis* (rice stem borer), *Locusta migratoria* (locust), *Chortiocetes terminifera* (locust), *Diabrotica* spp., (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp., (flat mites), *Boophilus microplus* (cattle tick), *Dermacentor variabilis* (American dog tick), *Ctenocephalides felis* (cat flea), *Liriomyza* spp., (leafminer), *Musca domestica* (housefly), *Aedes aegypti* (mosquito), *Anopheles* spp., (mosquitoes), *Culex* spp., (mosquitoes), *Lucillia* spp., (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp., and *Linognathus* spp., (biting and sucking lice), *Meloidogyne* spp., (root knot nematodes), *Globodera* spp., and *Heterodera* spp., (cyst nematodes), *Pratylenchus* spp., (lesion nematodes), *Rhodopholus* spp., (banana burrowing nematodes), *Tylenchulus* spp. (citrus nematodes), *Haemonchus contortus* (barber pole worm), *Caenorhabditis elegans* (vinegar eelworm), *Trichostrongylus* spp., (gastro intestinal nematodes) and *Deroceras reticulatum* (slug).

The compounds of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used on soybean to control, for example, *Elasmopalpus lignosellus, Diloboderus abderus, Diabrotica speciosa, Sternechus subsignatus, Formicidae, Agrotis ipsilon, Julus* spp., *Anticarsia gemmatalis, Megascelis* spp., *Procornitermes* spp., *Gryllotalpidae, Nezara viridula, Piezodorus* spp., *Acrosternum* spp., *Neomegalotomus* spp., *Cerotoma trifurcata, Popillia japonica, Edessa* spp., *Liogenys fuscus, Euchistus heros, stalk borer, Scaptocoris castanea, phyllophaga* spp., *Pseudoplusia includens, Spodoptera* spp., *Bemisia tabaci, Agriotes* spp., The compounds of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* spp.

The compounds of the invention may be used on corn to control, for example, *Euchistus heros, Dichelopsfurcatus, Diloboderus abderus, Elasmopalpus lignosellus, Spodoptera frugiperda, Nezara viridula, Cerotoma trifurcata, Popilliajaponica, Agrotis ypsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *Thrips* spp., *phyllophaga* spp., *scaptocoris* spp., *Liogenys fuscus, Spodoptera* spp., *Ostrinia* spp., *Sesamia* spp., *Agriotes* spp. The compounds of the invention are preferably used on corn to control *Euchistus heros, Dichelopsfurcatus, Diloboderus abderus, Nezara viridula, Cerotoma trifurcata, Popillia japonica, Diabrotica speciosa, Diabrotica virgifera, Tetranychus* spp., *Thrips* spp., *Phyllophaga* spp., *Scaptocoris* spp., *Agriotes* spp.

The compounds of the invention may be used on sugar cane to control, for example, *Sphenophorus* spp., termites, *Mahanarva* spp. The compounds of the invention are preferably used on sugar cane to control termites, *Mahanarva* spp.

The compounds of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp., *Spodoptera* spp., *Trichoplusia ni*. The compounds of the invention are preferably used on alfalfa to control *Hypera brunneipennis, Hypera postica, Empoasca solana, Epitrix, Lygus hesperus, Lygus lineolaris, Trichoplusia ni*.

The compounds of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana, Thrips* spp., *Spodoptera* spp., *Delia* spp. The compounds of the invention are preferably used on brassicas to control *Plutella xylostella, Pieris* spp., *Plusia* spp., *Trichoplusia ni, Phyllotreta* spp., *Thrips* spp.

The compounds of the invention may be used on oil seed rape, e.g. canola, to control, for example, *Meligethes* spp., *Ceutorhynchus napi, Psylloides* spp.

The compounds of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp. The compounds of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The compounds of the invention may be used on cotton to control, for example, *Anthonomus grandis, Pectinophora* spp., *heliothis* spp., *Spodoptera* spp., *Tetranychus* spp., *Empoasca* spp., *Thrips* spp., *Bemisia tabaci, Lygus* spp., *phyllophaga* spp., *Scaptocoris* spp. The compounds of the invention are preferably used on cotton to control *Anthonomus grandis, Tetranychus* spp., *Empoasca* spp., *Thrips* spp., *Lygus* spp., *phyllophaga* spp., *Scaptocoris* spp.

The compounds of the invention may be used on rice to control, for example, *Leptocorisa* spp., *Cnaphalocrosis* spp., *Chilo* spp., *Scirpophaga* spp., *Lissorhoptrus* spp., *Oebalus pugnax*. The compounds of the invention are preferably used on rice to control *Leptocorisa* spp., *Lissorhoptrus* spp., *Oebalus pugnax*.

The compounds of the invention may be used on coffee to control, for example, *Hypothenemus Hampei, Perileucoptera Coffeella, Tetranychus* spp., The compounds of the invention are preferably used on coffee to control *Hypothenemus Hampei, Perileucoptera Coffeella*.

The compounds of the invention may be used on citrus to control, for example, *Panonychus citri, Phyllocoptruta oleivora, Brevipalpus* spp., *Diaphorina citri, Scirtothrips* spp., *Thrips* spp., *Unaspis* spp., *Ceratitis capitata, Phyllocnistis* spp. The compounds of the invention are preferably used on citrus to control *Panonychus citri, Phyllocoptruta oleivora, Brevipalpus* spp, *Diaphorina citri, Scirtothrips* spp., *Thrips* spp., *Phyllocnistis* spp.

The compounds of the invention may be used on almonds to control, for example, *Amyelois transitella, Tetranychus* spp.

The compounds of the invention may be used on fruiting vegetable, including tomatoes, pepper, chili, eggplant, cucumber, squash etc, to control *Thrips* spp, *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., *Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. The compounds of the invention are preferably used on fruiting vegetable, including tomatoes, pepper, chili, eggplant, cucumber, squash etc, to control, for example, *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The compounds of the invention may be used on tea to control, for example, *Pseudaulacaspis* spp., *Empoasca* spp., *Scirtothrips* spp., *Caloptilia theivora*. The compounds of the invention are prefferably used on tea to control *Empoasca* spp., *Scirtothrips* spp.

The compounds of the invention may be used on bulb vegetables, including onion, leek etc to control, for example, *Thrips* spp., *Spodoptera* spp., *heliothis* spp. The compounds of the invention are preferably used on bulb vegetables, including onion, leek etc to control *Thrips* spp.

The compounds of the invention may be used on grapes to control, for example, *Empoasca* spp., *Lobesia* spp., *Frankliniella* spp., *Thrips* spp., *Tetranychus* spp., *Rhipiphorothrips Cruentatus, Eotetranychus Willamettei, Erythroneura Elegantula, Scaphoides* spp. The compounds of the invention are preferably used on grapes to control *Frankliniella* spp., *Thrips* spp., *Tetranychus* spp., *Rhipiphorothrips Cruentatus, Scaphoides* spp.

The compounds of the invention may be used on pome fruit, including apples, perars etc, to control, for example, *Cacopsylla* spp., *Psylla* spp., *Panonychus ulmi, Cydia pomonella*. The compounds of the invention are preferably used on pome fruit, including apples, pears etc, to control *Cacopsylla* spp., *Psylla* spp., *Panonychus ulmi*.

The compounds of the invention may be used on stone fruit to control, for example, *Grapholita molesta, Scirtothrips* spp., *Thrips* spp., *Frankliniella* spp., *Tetranychus* spp. The compounds of the invention are preferably used on stone fruit to control *Scirtothrips* spp., *Thrips* spp., *Frankliniella* spp., *Tetranychus* spp. The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkypyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a nonhuman animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE19520936.

The compounds of the invention may be used in combination with derivatives and analogues of the general class of dioxomorpholine antiparasitic agents as described in WO9615121 and also with anthelmintic active cyclic depsipeptides such as those described in WO-9611945, WO-9319053, WO-9325543, EP-626375, EP-382173, WO-9419334, EP382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means one specific compound selected from Table 1 to 126 or Table B), which may result in a synergistic combination with the given active ingredient): imidacloprid+Tx, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, fipronil+Tx, ivermectin+Tx, omeprazole+Tx, tiamulin+Tx, benazepril+Tx, milbemycin+Tx, cyromazine+Tx, thiamethoxam+Tx, pyriprole+Tx, deltamethrin+Tx, cefquinome+Tx, florfenicol+Tx, buserelin+Tx, cefovecin+Tx, tulathromycin+Tx, ceftiour+Tx, selamectin+Tx, carprofen+Tx, metaflumizone+Tx, moxidectin+Tx, methoprene (including S-methoprene)+Tx, clorsulon+Tx, pyrantel+Tx, amitraz+Tx, triclabendazole+Tx, avermectin+Tx, abamectin+Tx, emamectin+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, fipronil+Tx, lufenuron+Tx, ecdysone+Tx or tebufenozide+Tx; more preferably, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx, pyrantel+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, lufenuron+Tx or ecdysone+Tx; even more preferably enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx or pyrantel+Tx.

Examples of ratios include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on the other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the compounds of the invention allows more economic and simple husbandry of animals.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are

*Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp., and *Aedes* spp.

Mites include *Mesostigmalphatalpha* spp., e.g., *mesostigmatids* such as the chicken mite, *Dermalphanyssus galphallinalphae*; itch or scab mites such as *Sarcoptidae* spp., for example, *Salpharcoptes scalphabiei*; mange mites such as *Psoroptidae* spp., including *Chorioptes bovis* and *Psoroptes ovis*; chiggers e.g., *Trombiculidae* spp., for example the North American chigger, *Trombiculalpha alphalfreddugesi.*

Ticks include, e.g., soft-bodied ticks including *Argasidae* spp., for example *Argalphas* spp., and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp., (including the former *Boophilus* genera).

Lice include, e.g., sucking lice, e.g., *Menopon* spp. and *Bovicola* spp.; biting lice, e.g., *Haematopinus* spp., *Linognathus* spp., and *Solenopotes* spp.

Fleas include, e.g., *Ctenocephalides* spp., such as dog flea (*Ctenocephalides canis*) and cat flea (*Ctenocephalides felis*); *Xenopsylla* spp., such as oriental rat flea (*Xenopsylla cheopis*); and *Pulex* spp., such as human flea (*Pulex irritans*).

True bugs include, e.g., *Cimicidae* or e.g., the common bed bug (*Cimex lectularius*); *Triatominae* spp., including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites including: flies such as *Haematobia* (*Lyperosia*) *irritans* (horn fly), *Simulium* spp., (blackfly), *Glossina* spp., (tsetse flies), *Hydrotaea irritans* (head fly), *Musca autumnalis* (face fly), *Musca domestica* (house fly), *Morellia simplex* (sweat fly), *Tabanus* spp., (horse fly), *Hypoderma bovis, Hypoderma lineatum, Lucilia sericata, Lucilia cuprina* (green blowfly), *Calliphora* spp., (blowfly), *Protophormia* spp., *Oestrus ovis* (nasal botfly), *Culicoides* spp., (midges), *Hippobosca equine, Gastrophilus intestinalis, Gastrophilus haemorrhoidalis* and *Gastrophilus nasalis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp., and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount.

Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates.

Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are know, e.g. from Handbuch Textilveredlung: Band 1: Ausrüstung, Band 2: Farbgebung, Band 3: Beschichtung, Band 4: Umwelttechnik; Verlag: Deutscher Fachverlag; Auflage: 15, überarbeitete Ausgabe (17. Apr. 2006); ISBN-10: 3866410123; ISBN-13: 978-3866410121, see especially Band 1: Ausrüstung pages 27-198, more preferably on page 118; or WO2008151984 or WO2003034823 or U.S. Pat. No. 5,631,072 or WO200564072 or WO2006128870 or EP1724392 or WO2005064072 or WO2005113886 or WO2007090739.

The term "plant" as used herein includes seedlings, bushes and trees. The term "crops" or "plant" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp., or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMGCOA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* spp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one specific compound selected from Table 1 to 126 or Table B of the present invention"):
an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acri*-

*dum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, normbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole 10 [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5 S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, 3-difluoromethyl-1-methyl-1H-pyrazole-4-carboxylic acid (3',4',5'-trifluoro-biphenyl-2-yl)-amide (disclosed in WO 2006/0873 43)+TX, and 1-methyl-2-(2,4,5-trichloro-thiophen-3-yl)-ethyl]+TX.

The references in brackets behind the active ingredients, e.g. [3878-19-1] refer to the Chemical Abstracts Registry number. The above described mixing partners are known.

Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I or one specific compound selected from Table 1 to 126 or Table B, and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on the other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I or one specific compound selected from Table 1 to 126 or Table B and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I or one specific compound selected from Table 1 to 126 or Table B and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

The compounds of formula (I) according to the invention can also be used in combination with safeners. Preferably, in these mixtures, the compound of the formula (I) or one specific compound selected from Table 1 to 126 or Table B. The following mixtures with safeners, especially, come into consideration:

compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecoprop and compound of the formula (I)+mecoprop-P.

The mixing partners of the TX may also be in the form of esters or salts, as mentioned e.g. in The Pesticide Manual, 12th Edition (BCPC), 2000.

In the above different lists of active ingredients to be mixed with a TX, the compound of the formula I is preferably one specific compound selected from Table 1 to 126 or Table B.

In the above-mentioned mixtures of compounds of formula I, in particular one specific compound selected from Table 1 to 126 or Table B, with other insecticides, fungicides, herbicides, safeners, adjuvants and the like, the mixing ratios can vary over a large range and are, preferably 100:1 to 1:6000, especially 50:1 to 1:50, more especially 20:1 to 1:20, even more especially 10:1 to 1:10. Those mixing ratios are understood to include, on the one hand, ratios by weight and also, on the other hand, molar ratios.

The mixtures can advantageously be used in the abovementioned formulations (in which case "active ingredient" relates to the respective mixture of TX with the mixing partner).

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The mixtures comprising a TX one specific compound selected from Table 1 to 126 or Table B, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

PREPARATION EXAMPLES

Examples

The following abbreviations were used throughout this section: s=singlet; bs=broad singlet; d=doublet; dd=double doublet; dt=double triplet; t=triplet; tt=triple triplet; q=quartet, sept=septet; m=multiplet; Me=methyl; Et=ethyl; Pr=propyl; Bu=butyl; M.p.=melting point; EtOAc=Ethyl acetate; TBME=tert-butyl methyl ether Example P1: N-[3-[[2-bromo-4-[1-[bromo(difluoro) methyl]-1,2,2,2-tetrafluoro-ethyl]-6-chloro-phenyl] carbamoyl]-2-methoxy-phenyl]pyridine-4-carboxamide (Entry 3 of Table B)

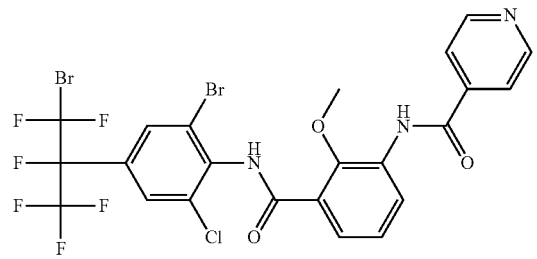 [SMILES: COc1c(NC(=O)c2ccncc2)cccc1C(=O)Nc1c(Cl)cc(C(F)(C(F)(F)F)C(F)(F)Br)cc1Br]

Step 1: 4-[1-[bromo(difluoro)methyl]-1,2,2,2-tetrafluoro-ethyl]aniline

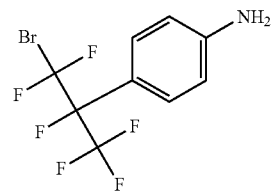 [SMILES: Nc1ccc(C(F)(C(F)(F)F)C(F)(F)Br)cc1]

Aniline (40 g, 425 mmol) was dissolved in 670 ml TBME and 470 ml water. and treated with sodium dithionite (102 g, 510 mmol), tetrabutylammonium hydrogen sulphate (11.6 g, 34 mmol), and Sodium bicarbonate (42.9 g, 510 mmol, 1.2 eq.). The yellow emulsion was treated drop wise with 1,2-Dibromo-1,1,2,3,3,3-hexafluoro-propane (72.9 ml, 510 mmol, prepared as described in Eur. Pat. Appl., 1418163) keeping the temperature below 250° C. during vigorous stirring. After the addition the reaction was allowed to stir for a further 3 hr, the organic phase separated and the water phase back extracted with (×3) with tert-butyl methyl ether. The combined organic phases were washed with brine, dried over anhydrous MgSO$_4$, filtrated and concentrated in vacuo to give 46 g (33%) of the title compound as dark brownish oil that was used in the next step without further purification.

$^1$H NMR (400 MHz, CDCl$_3$, δ in ppm): 7.36-7.43 (d, J=8.4 Hz, 1H); 6.78 (d, J=8.4 Hz, 1H); 4.14 (br. s., 2H)

Step 2: 2-bromo-4-[1-[bromo(difluoro)methyl]-1,2,2,2-tetrafluoro-ethyl]aniline

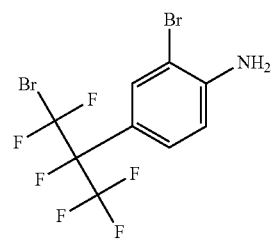 [SMILES: Nc1ccc(C(F)(C(F)(F)F)C(F)(F)Br)cc1Br]

4-[1-[Bromo(difluoro)methyl]-1,2,2,2-tetrafluoro-ethyl] aniline (46.0 g, 136 mmol) was dissolved in DMF (370 ml) and treated portion wise with N-bromosuccinimide (25.1 g, 138 mmol) whilst keeping the reaction temperature below 30° C. The mixture was allowed to stir at rt until TLC analysis after 3 hr showed reaction completion. The reaction mixture was diluted with TBME and water, the organic phase separated, and the aqueous phase back extracted with 2×100 ml tert-butyl methyl ether. The combined organic phases were washed with water, brine, dried over $Na_2SO_4$, filtrated and concentrated in vacuo. This gave 62 g of the title compound (containing a small amount of DMF) as a brown oil that was used in the next step without further purification.

$^1$H NMR (400 MHz, $CDCl_3$, δ in ppm): 7.64 (s, 1H); 7.32 (d, J=8.4 Hz, 1H); 6.81 (d, J=8.4 Hz, 1H); 3.36 (br s, 2H).

Step 3: 2-bromo-4-[1-[bromo(difluoro)methyl]-1,2,2,2-tetrafluoro-ethyl]-6-chloro-aniline

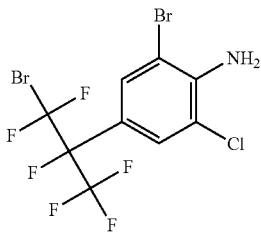 [SMILES: Nc1c(Cl)cc(C(F)(C(F)(F)F)C(F)(F)Br)cc1Br]

A solution of 2-bromo-4-[1-[bromo(difluoro)methyl]-1,2,2,2-tetrafluoro-ethyl]aniline (62 g, 139 mmol) in DMF (450 ml) was treated with N-chlorosuccinimide (19.9 g, 146 mmol) and the mixture was heated to 70° C. LCMS after 2 hr showed reaction completion. The reaction mixture was diluted with TBME and water, the organic phase separated, and the aqueous phase back extracted with 2×100 ml TBME. The combined organic phases were washed with water, brine, dried over $Na_2SO_4$, filtered and concentrated in vacuo to give 59.2 g of a brown oil that was purified over a silica gel cartridge (Torrent) eluting with 100:0→50:50 heptane/EtOAc. This gave the title compound (46 g, 76%) as a pale brown oil.

$^1$H NMR (400 MHz, $CDCl_3$, δ in ppm): 7.60 (s, 1H); 7.46 (s, 1H); 4.78 (br. s., 2H).

Step 4: N-[2-bromo-4-[1-[bromo(difluoro)methyl]-1,2,2,2-tetrafluoro-ethyl]-6-chloro-phenyl]-2-fluoro-3-nitro-benzamide

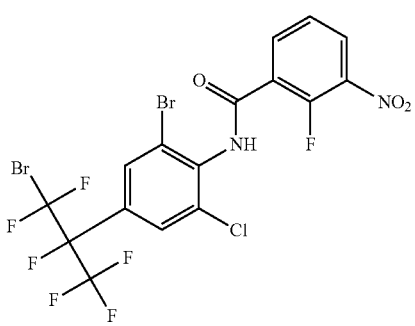 [SMILES: O=C(Nc1c(Cl)cc(C(F)(C(F)(F)F)C(F)(F)Br)cc1Br)c1cccc([N+](=O)[O-])c1F]

A solution of 2-bromo-4-[1-[bromo(difluoro)methyl]-1,2,2,2-tetrafluoro-ethyl]-6-chloro-aniline (46 g, 104 mmol) and potassium iodide (4.3 g, 25.9 mmol) were dissolved in acetonitrile (460 ml). To this solution was added 2-fluoro-3-nitro-benzoyl chloride (45.8 g, 207 mmol, prepared as described in J. Amer. Chem. Soc, 135(26), 9675, 2013) and the mixture heated to 82° C. over night. LCMS after this time showed reaction completion. The mixture was diluted with 400 ml dichloromethane, quenched with $NaHSO_3$ sol. and extracted with 2×250 ml dichloromethane. The combined organic layers were washed with brine, dried over $Na_2SO_4$, filtrated and evaporated to give 86 g of crude product as a yellow resin. Purification over silica gel cartridge (Torrent) eluting with Heptane/EtOAc 100:0→50:50 gave 62 g (100%) of the title compound as pale yellow crystals.

$^1$H NMR (400 MHz, $CDCl_3$, δ in ppm): 8.44-8.54 (m, 1H); 8.28 (td, J=7.7, 1.8 Hz, 1H), 8.14 (d, J=12.1 Hz, 1H); 7.86 (s, 1H), 7.74 (s, 1H), 7.53 (t, J=8.1 Hz, 1H).

LCMS: (Method ZDQ13): 599, 601 (M+H), 603, retention time 1.17 min.

Step 5: N-[2-bromo-4-[1-[bromo(difluoro)methyl]-1,2,2,2-tetrafluoro-ethyl]-6-chloro-phenyl]-2-methoxy-3-nitro-benzamide

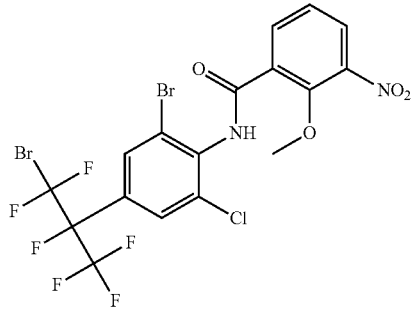 [SMILES: COc1c(C(=O)Nc2c(Cl)cc(C(F)(C(F)(F)F)C(F)(F)Br)cc2Br)cccc1[N+](=O)[O-]]

A solution of N-[2-bromo-4-[1-[bromo(difluoro)methyl]-1,2,2,2-tetrafluoro-ethyl]-6-chloro-phenyl]-2-fluoro-3-nitro-benzamide (62 g, 102 mmol) was dissolved in MeOH (450 ml) and treated with a solution of sodium methoxide in methanol (5.4 mol/L, 29 ml, 158 mmol) at rt. The mixture was allowed to stir at rt until LCMS/TLC showed reaction completion. The reaction mixture was diluted with 100 ml of water and stirred for 6 hr at rt. Then the mixture was evaporated, the residue was dissolved in EtOAc, and the EtOAc solution washed with brine, the organic layer dried over $Na_2SO_4$, filtered, and concentrated in vacuo. The crude product was used in the next step without further purification.

$^1$H NMR ($CDCl_3$, 400 MHz): δ (ppm) 9.22 (s, 1H); 8.45 (dd, J=7.7, 1.8 Hz, 1H); 8.08 (dd, J=8.1, 1.8 Hz, 1H); 7.86 (s, 1H); 7.74 (s, 1H); 7.45 (t, J=8.1 Hz, 1H); 7.27 (s, 1H); 4.12 (s, 3H).

LCMS: (Method ZDQ13): 611, 613 (M+H), 615, retention time 1.18 min.

Step 6: 3-amino-N-[2-bromo-4-[1-[bromo(difluoro)methyl]-1,2,2,2-tetrafluoro-ethyl]-6-chloro-phenyl]-2-methoxy-benzamide

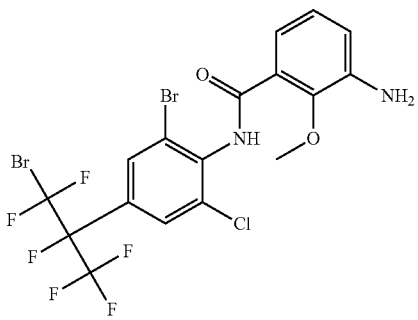 [SMILES: COc1c(N)cccc1C(=O)Nc1c(Cl)cc(C(F)(C(F)(F)F)C(F)(F)Br)cc1Br]

N-[2-bromo-4-[1-[bromo(difluoro)methyl]-1,2,2,2-tetrafluoro-ethyl]-6-chloro-phenyl]-2-methoxy-3-nitro-benzamide (5.6 g, 8.4 mmol) dissolved in iso-propanol (120 ml) was treated with anhydrous tin chloride (5.7 g, 30 mmol) and then dropwise with concentrated hydrochloric acid (8 ml) at rt. The mixture was then heated to 90° C. for 1 hr after which LCMS/TLC showed reaction completion. The mixture was poured on water, adjusted to pH10 with 2N NaOH and extracted with 3×100 ml EtOAc. The combined organic layers were washed with brine, dried over MgSO$_4$, filtrated and concentrated in vacuo. Purification by over a silica gel cartridge (Rf200) eluting with Cyclohexane/EtOAc 95:5→60:40 gave the title compound (4.6 g, 94%) as a brownish resin:

$^1$H NMR (400 MHz, CDCl$_3$, δ in ppm): 9.53 (s, 1H); 7.84 (s, 1H); 7.72 (s, 1H), 7.59 (dd, J=7.7, 1.8 Hz, 1H); 7.12 (t, J=7.7 Hz, 1H); 7.01 (dd, J=7.9, 1.7 Hz, 1H); 4.18 (br. s., 2H); 4.01 (s, 3H).

LCMS: (Method ZDQ13): 583, 585 (M+H), 587, retention time 1.14 min.

Step 7: N-[3-[[2-bromo-4-[1-[bromo(difluoro)methyl]-1,2,2,2-tetrafluoro-ethyl]-6-chloro-phenyl]carbamoyl]-2-methoxy-phenyl]pyridine-4-carboxamide

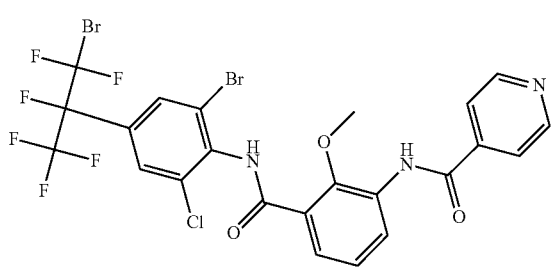 [SMILES: COc1c(NC(=O)c2ccncc2)cccc1C(=O)Nc1c(Cl)cc(C(F)(C(F)(F)F)C(F)(F)Br)cc1Br]

To a solution of 3-amino-N-[2-bromo-4-[1-[bromo(difluoro)methyl]-1,2,2,2-tetrafluoro-ethyl]-6-chloro-phenyl]-2-methoxy-benzamide (83 mg, 0.14 mmol) and Pyridine (45 μl, 0.55 mmol) in THF (4 ml) was added pyridine-4-carbonyl chloride hydrochloride (28 mg, 0.15 mmol) The mixture was stirred at rt and monitored by TLC/LCMS. After 23 hr, there was still about 20% of starting material present and thus, additional pyridine-4-carbonyl chloride hydrochloride (25 mg, 0.14 mmol) was added. Upon reaction completion, the mixture was quenched with water and sat. NaHCO$_3$-sol, and extracted with 2×20 ml EtOAc. The combined organic layers was washed with brine, dried over Na$_2$SO$_4$, filtrated and concentrated in vacuo.

The crude product was purified over silica gel cartridge (Rf200) eluting with Cyclohexane/EtOAc 10:90→0:100 to give the title compound (87 mg, 93%) as a pale yellow resin.

$^1$H NMR (400 MHz, CDCl$_3$, δ in ppm): 9.03 (s, 1H); 8.89 (d, J=4.9 Hz, 2H); 8.69 (dd, J=8.1, 1.5 Hz, 1H); 8.51 (s, 1H); 7.96 (dd, J=7.9, 1.7 Hz, 1H); 7.86 (s, 1H); 7.74-7.81 (m, 3H); 7.41 (t, J=8.1 Hz, 1H); 4.09 (s, 3H).

LCMS: (Method ZDQ13): 688, 690 (M+H), 692, retention time 1.10 min.

Example P2: Step 2: N-[2-bromo-4-[1-[bromo(difluoro)methyl]-1,2,2,2-tetrafluoro-ethyl]-6-chloro-phenyl]-3-[(4-cyanobenzoyl)-ethyl-amino]-2-methoxy-benzamide (Entry 1 of Table B)

Step 1: N-[2-bromo-4-[1-[bromo(difluoro)methyl]-1,2,2,2-tetrafluoro-ethyl]-6-chloro-phenyl]-3-(ethyl-amino)-2-methoxy-benzamide

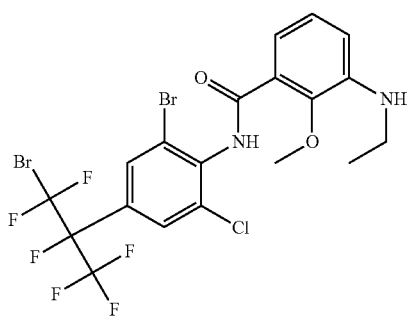 [SMILES: CCNc1cccc(C(=O)Nc2c(Cl)cc(C(F)(C(F)(F)F)C(F)(F)Br)cc2Br)c1OC]

A solution of N-[2-bromo-4-[1-[bromo(difluoro)methyl]-1,2,2,2-tetrafluoro-ethyl]-6-chloro-phenyl]-2-methoxy-3-nitro-benzamide (5.0 g, 8.1 mmol, step 6, Example P1), acetaldehyde (0.61 ml, 10.6 mmol), and acetic aid (0.61 ml, 10.6 mmol) in MeOH (100 ml), was treated with sodium cyanoborohydride (699 mg, 10.6 mmol) at rt. The resulting mixture was stirred at rt and after 4 hr LCMS shows full conversion. The mixture was concentrated in vacuo, and the residue was quenched with 25 ml water and extracted 3×50 ml of dichloromethane. The combined organic layers was washed with water, brine, dried over Na$_2$SO$_4$, filtrated concentrated in vacuo. Purification over a silica gel cartridge (Rf200) eluting with dichloromethane/MeOH gave the title compound (4.8 g, 96%) as off white crystals.

$^1$H NMR (400 MHz, CDCl$_3$, δ in ppm): 9.49 (s, 1H); 7.84 (s, 1H); 7.72 (s, 1H); 7.48 (dd, J=7.7, 1.5 Hz, 1H); 7.18 (t, J=7.9 Hz, 1H); 6.89 (dd, J=8.1, 1.5 Hz, 1H); 4.17 (br. s., 1H); 3.97 (s, 3H); 3.24 (q, J=7.0 Hz, 2H); 1.35 (t, J=7.2 Hz, 3H).

LCMS: (Method ZDQ13): 611, 613 (M+H), 615, retention time 1.27 min

Step 2: N-[2-bromo-4-[1-[bromo(difluoro)methyl]-1,2,2,2-tetrafluoro-ethyl]-6-chloro-phenyl]-3-[(4-cyanobenzoyl)-ethyl-amino]-2-methoxy-benzamide

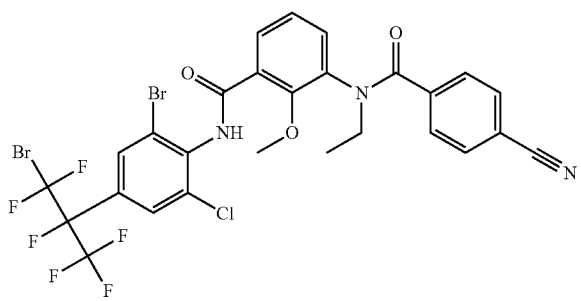 [SMILES: CCN(C(=O)c1ccc(C#N)cc1)c1cccc(C(=O)Nc2c(Cl)cc(C(F)(C(F)(F)F)C(F)(F)Br)cc2Br)c1OC]

4-cyanobenzoyl chloride (105 mg, 0.615 mmol) was added to a solution of N-[2-bromo-4-[1-[bromo(difluoro)methyl]-1,2,2,2-tetrafluoro-ethyl]-6-chloro-phenyl]-3-(ethylamino)-2-methoxy-benzamide (353 mg, 0.559 mmol) and Pyridine (1831, 2.24 mmol) in THF (15 ml). The mixture was stirred at rt and monitored by TLC/LCMS. Upon reaction completion, the reaction mixture was quenched with water and sat. NaHCO$_3$-sol, and extracted with 2×20 ml EtOAc. The combined organic layers were washed with brine, dried over Na$_2$SO$_4$, filtrated and evaporated.

Purification over a silica gel cartridge (Rf200) eluting with Cyclohexane/EtOAc 100:0→60:40, gave the title compound (368 mg, 89%) as a white foam.

$^1$H NMR (400 MHz, CDCl$_3$, δ in ppm): Selected signals, rotamer mixture: 8.05 (d, J=7.7 Hz); 7.81 (s), 7.70 (s); 7.38-7.63 (m), 3.52-4.57 (m); 1.11-1.69 (m).

LCMS: (Method ZDQ13): 740, 742 (M+H), 744, retention time 1.20 min

Example P3: N-[3-[[2-bromo-4-[1-[chloro(difluoro)methyl]-1,2,2,2-tetrafluoro-ethyl]-6-(difluoromethoxy)phenyl]carbamoyl]-2-methoxy-phenyl]-N-ethyl-1-oxido-pyridin-1-ium-4-carboxamide (Entry 44 of the table B)

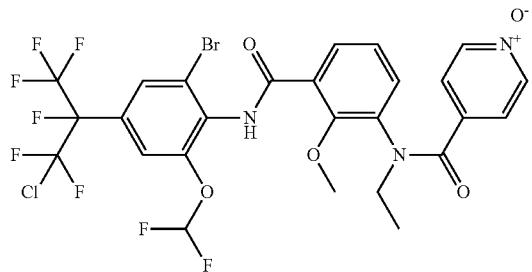

A colourless solution of N-[3-[[2-bromo-4-[1-[chloro(difluoro)methyl]-1,2,2,2-tetrafluoro-ethyl]-6-(difluoromethoxy)phenyl]carbamoyl]-2-methoxy-phenyl]-N-ethyl-pyridine-4-carboxamide (Entry 36 of the table B) (0.095 g) in dichloromethane (3.0 ml) was treated with 0.040 g of 70% meta-chloroperbenzoic acid. After 16 hours stirring at 20° C., full conversion was observed by LC-MS and TLC analyses. The reaction mixture was washed with an aqueous solution of sodium sulfite, and then twice with an aqueous solution of sodium bicarbonate. The organic phase was dried over sodium sulfate and evaporated to yield the title compound as a white powder with a melting range of 109-228° C.

$^1$H NMR (400 MHz, CDCl$_3$, δ in ppm): 8.60 (br.s, 1H), 8.05 (d, J=8.1 Hz, 1H), 7.97 (br. d, 2H), 7.78 (s, 1H), 7.53 (d, J=8.1 Hz, 1H), 7.49 (s, 1H), 7.8 (t, J=8.1 Hz, 1H), 7.20 (br. d, 2H), 6.61 (t, J=73 Hz, 1H), 4.30 (br. m, 1H), 3.91 (s, 3H), 3.75 (br. m, 1H), 1.41 (br. t, 3H).

Example P4: N-[3-[[2-bromo-6-(difluoromethoxy)-4-[1,2,2,2-tetrafluoro-1-(trifluoromethyl) ethyl]phenyl]carbamoyl]-2-methoxy-phenyl]-N-methyl-pyridine-4-carboxamide (Entry 36 of the table B)

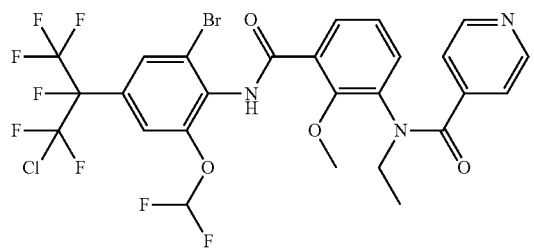 [SMILES: CCN(C(=O)c1ccncc1)c1cccc(C(=O)Nc2c(Br)cc(C(F)(C(F)(F)F)C(F)(F)Cl)cc2OC(F)F)c1OC]

Step 1: 4-[1-[chloro(difluoro)methyl]-1,2,2,2-tetrafluoro-ethyl]-2-(difluoromethoxy)aniline

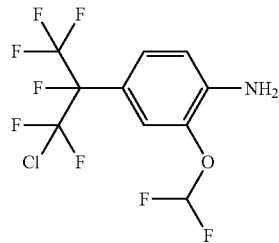 [SMILES: Nc1ccc(C(F)(C(F)(F)F)C(F)(F)Cl)cc1OC(F)F]

A solution of 2-difluoromethoxyaniline (4.5 g) in a mixture of 2-methoxy-2-methyl-propane (41 ml) and water (41 ml) was stirred at 20° C. Sodium hydrosulfite (6.8 g), sodium bicarbonate (2.8 g) and tetrabutylammonium hydrogensulfate (0.69 g) followed by 1-chloro-1,1,2,3,3,3-hexafluoro-2-iodo-propane (preparation described in Patent FR 1337264) (10.0 g) were added. Gas evolution was observed during the first 4 hours. The mixture was stirred for 3 days, after which time the phases were separated. The aqueous phase was extracted twice with 2-methoxy-2-methyl-propane and the combined organic phases were washed twice with 1 molar aqueous hydrochloric acid (100 ml) followed by two washing with water (100 ml), then brine (100 ml). The organic phase was dried over sodium sulfate and the solvent removed under reduced pressure to yield 4-[1-[chloro (difluoro)methyl]-1,2,2,2-tetrafluoroethyl]-2-(difluoromethoxy)aniline as orange oil that was used in the following step without further purification.

$^1$H NMR (400 MHz, CDCl$_3$, δ in ppm): 7.29 (m, 2H), 6.84 (d, J=8.1 Hz, 1H), 6.49 (t, J=73 Hz, 1H), 4.15 (br. s, 2H).

Step 2: 2-bromo-4-[1-[chloro(difluoro)methyl]-1,2,
2,2-tetrafluoro-ethyl]-6-(difluoromethoxy)aniline

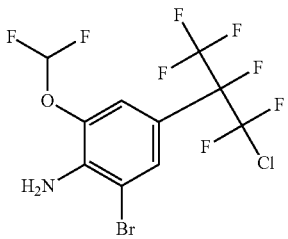 [SMILES: Nc1c(Br)cc(C(F)(C(F)(F)F)C(F)(F)Cl)cc1OC(F)F]

To an orange solution of 4-[1-[chloro(difluoro)methyl]-1,2,2,2-tetrafluoro-ethyl]-2-(difluoromethoxy)aniline (3.88 g) (preparation described in step 1) in dichloromethane (24 ml) was added portion wise N-bromosuccinimid (2.41 g) under stirring at 20° C. The reaction mixture became dark brown. The reaction was complete after 1 hour (LC-MS analysis). To the reaction mixture was added, under stirring, an aqueous solution of sodium hydroxide (100 ml, 1 mole/l). After separation of the phases, the organic phase was washed with another 100 ml portion of 0.1 M sodium hydroxide. The combined aqueous phases were extracted twice with 100 ml dichloromethane. The organic layers were joined, dried over sodium sulfate and the solvent removed under reduced pressure, leaving 2-bromo-4-[1-[chloro(difluoro)methyl]-1,2,2,2-tetrafluoro-ethyl]-6-(difluoromethoxy)aniline as brown oil that was used in the following step without further purification.

$^1$H NMR (400 MHz, CDCl$_3$, δ in ppm): 7.55 (s, 1H), 7.25 (s, 1H), 6.60 (t, J=72.7 Hz, 1H), 4.60 (br. s, 2H).

Step 3: N-[2-bromo-4-[1-[chloro(difluoro)methyl]-1,2,2,2-tetrafluoro-ethyl]-6-(difluoromethoxy)phenyl]-2-fluoro-3-nitro-benzamide

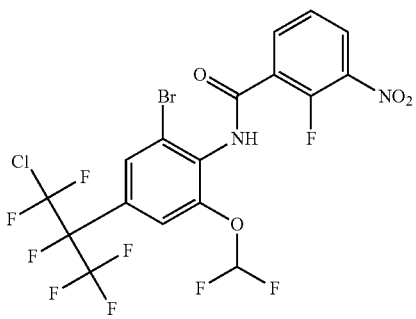 [SMILES: O=C(Nc1c(Br)cc(C(F)(C(F)(F)F)C(F)(F)Cl)cc1OC(F)F)c1cccc([N+](=O)[O-])c1F]

A solution of 2-bromo-4-[1-[chloro(difluoro)methyl]-1,2,2,2-tetrafluoro-ethyl]-6-(difluoromethoxy)aniline (4.38 g) (preparation described in step 2) in acetonitrile (25 ml) was treated with powdered potassium iodide (0.172 g) followed by a solution of 2-fluoro-3-nitro-benzoyl chloride (2.53 g) in acetonitrile (20 ml). The resulting mixture was stirred under reflux for 20 hours. The reaction mixture was evaporated to dryness and the residue partitioned between dichloromethane and aqueous saturated sodium bicarbonate. The aqueous phase was extracted twice with dichloromethane and the combined organic phases were dried over sodium sulfate and evaporated. The residue was purified by flash chromatography over silica gel eluting with a mixture of ethyl acetate and heptanes. N-[2-bromo-4-[1-[chloro(difluoro)methyl]-1,2,2,2-tetrafluoro-ethyl]-6-(difluoromethoxy)phenyl]-2-fluoro-3-nitro-benzamide was isolated as solid melting at 125-127° C.

Step 4: N-[2-bromo-4-[1-[chloro(difluoro)methyl]-1,2,2,2-tetrafluoro-ethyl]-6-(difluoromethoxy)phenyl]-2-methoxy-3-nitro-benzamide

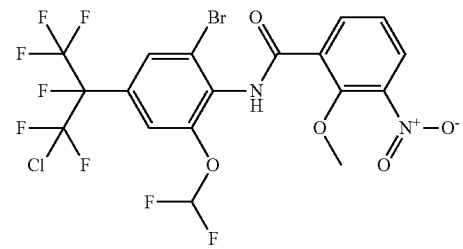 [SMILES: COc1c(C(=O)Nc2c(Br)cc(C(F)(C(F)(F)F)C(F)(F)Cl)cc2OC(F)F)cccc1[N+](=O)[O-]]

To a pale brown solution of N-[2-bromo-4-[1-[chloro(difluoro)methyl]-1,2,2,2-tetrafluoro-ethyl]-6-(difluoromethoxy)phenyl]-2-fluoro-3-nitro-benzamide (2.23 g) (preparation described in step 3) in methyl alcohol (35.6 ml) was added potassium carbonate (1.10 g) and the resulting suspension was heated to 50° C. under stirring for 4 hours. The reaction was complete and the reaction mixture was filtered. The filtrate was evaporated and the residue was partitioned between dichloromethane and water. The aqueous phase was extracted with dichloromethane and the organic solution was dried over sodium sulfate and evaporated to yield the desired compound as brown oil. It was used without further purification in the next step.

$^1$H NMR (400 MHz, CDCl$_3$, δ in ppm): 9.09 (s, 1H), 8.37 (dd, J=8.2 Hz, J=2 Hz, 1H), 8.05 (dd, J=8.2 Hz, J=2 Hz, 1H), 7.82 (s, 1H), 7.52 (s, 1H), 7.43 (t, J=8.2 Hz, 1H), 6.60 (t, J=73.5 Hz, 1H), 4.14 (s, 3H).

Step 5: 3-amino-N-[2-bromo-4-[1-[chloro(difluoro)methyl]-1,2,2,2-tetrafluoro-ethyl]-6-(difluoromethoxy)phenyl]-2-methoxy-benzamide

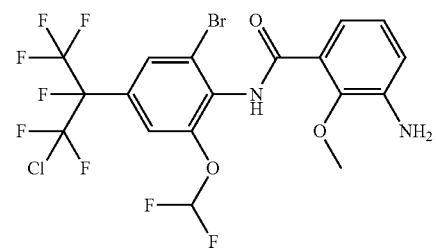 [SMILES: COc1c(N)cccc1C(=O)Nc1c(Br)cc(C(F)(C(F)(F)F)C(F)(F)Cl)cc1OC(F)F]

To a mixture of 2.306 g N-[2-bromo-4-[1-[chloro(difluoro)methyl]-1,2,2,2-tetrafluoro-ethyl]-6-(difluoromethoxy)phenyl]-2-methoxy-3-nitro-benzamide (preparation described in step 4), iron powder (0.535 g), ethyl alcohol (31 ml) and water (6 ml), was added 0.016 ml concentrated aqueous hydrochloric acid. The pale green suspension was heated to reflux temperature and became quickly brown. After stirring for two hours the reaction was complete (LC-MS and TLC analyses). The reaction mixture was filtered through a pad of celite and the solid residue washed with dichloromethane. The filtrate was evaporated and taken up in dichloromethane. The organic phase was dried over sodium sulfate and evaporated to yield the crude title compound as brown thick oil. This compound was used without further purification in the following step.

$^1$H NMR (400 MHz, CDCl$_3$, δ in ppm): 9.42 (br. s, 1H), 7.81 (s, 1H), 7.50 (m, 2H), 7.10 (t, J=8.2 Hz, 1H), 6.97 (d, J=8.2 Hz, 1H), 6.61 (t, J=73.5 Hz, 1H), 3.98 (s, 3H), 3.95 (s, broad, 2H).

Step 6: N-[2-bromo-4-[1-[chloro(difluoro)methyl]-1,2,2,2-tetrafluoro-ethyl]-6-(difluoromethoxy)phenyl]-3-(ethylamino)-2-methoxy-benzamide

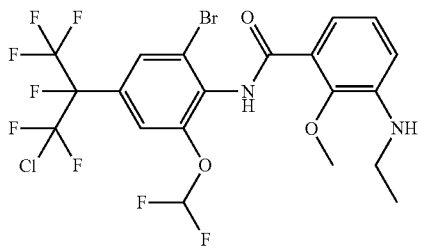 [SMILES: CCNc1cccc(C(=O)Nc2c(Br)cc(C(F)(C(F)(F)F)C(F)(F)Cl)cc2OC(F)F)c1OC]

To a solution of 1.411 g of 3-amino-N-[2-bromo-4-[1-[chloro(difluoro)methyl]-1,2,2,2-tetrafluoro-ethyl]-6-(difluoromethoxy)phenyl]-2-methoxy-benzamide (preparation described in step 5) in 20 ml methanol, 0.156 ml acetic acid and 0.109 g acetaldehyde were added, followed by 0.180 g of sodium cyanoborohydride. Gas evolution was observed. The reaction mixture was stirred at 20° C. for 17 hours. Then the solvent was evaporated and the residue was partitioned between dichloromethane and water. The aqueous phase was extracted twice with dichloromethane and the combined organic phases were dried over sodium sulfate and evaporated. The crude product was flash-chromatographed over silica gel using a gradient from 10% ethyl acetate in cyclohexane to 20% ethyl acetate in cyclohexane. The desired product was isolated as a colorless solid with a melting point of 121-123° C.

Step 7: N-[3-[[2-bromo-6-(difluoromethoxy)-4-[1,2,2,2-tetrafluoro-1-(trifluoromethyl) ethyl]phenyl]carbamoyl]-2-methoxy-phenyl]-N-methyl-pyridine-4-carboxamide (Entry 36 of the table B)

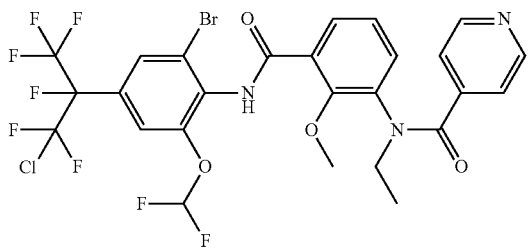

To a colorless solution of 0.300 g N-[2-bromo-4-[1-[chloro(difluoro)methyl]-1,2,2,2-tetrafluoro-ethyl]-6-(difluoromethoxy)phenyl]-3-(ethylamino)-2-methoxy-benzamide (preparation described in step 6) in 5.0 ml of tetrahydrofuran was added 138 mg of isonicotinoyl chloride hydrochloride. The suspension was heated to 70° C. for 1 hour. The reaction was complete, as shown by LC-MS and TLC analyses. The reaction mixture was concentrated under reduced pressure and the residue was dissolved in dichloromethane. The organic phase was washed with saturated aqueous sodium bicarbonate. The aqueous phase was back extracted twice with dichloromethane. The organic phases were combined and dried over sodium sulfate and evaporated. The crude product was chromatographed over silica gel eluting with a mixture of 50% ethyl acetate and 50% cyclohexane. After removal of the solvent, N-[3-[[2-bromo-6-(difluoromethoxy)-4-[1,2,2,2-tetrafluoro-1-(trifluoromethyl) ethyl]phenyl]carbamoyl]-2-methoxy-phenyl]-N-methyl-pyridine-4-carboxamide was obtained as a white powder with a melting range of 112-161° C.

$^1$H NMR (400 MHz, CDCl$_3$, δ in ppm): 8.50 (s, broad, 2H), 8.02 (t, 1H), 7.83 (d, 1H), 7.78 (s, 1H), 7.49 (s, 1H), 7.43 (t, 1H), 7.28 (t, 1H), 7.18 (s, broad, 2H), 6.55 (t, 1H), 4.00 (m, broad, 2H), 1.28 (t, broad, 3H).

Example P5: N-[3-[[2-bromo-6-chloro-4-[1-(difluoromethyl)-1,2,2,2-tetrafluoro-ethyl]phenyl]carbamoyl]-2-methoxy-phenyl]-N-ethyl-pyridine-4-carboxamide (Entry 51 of the table B)

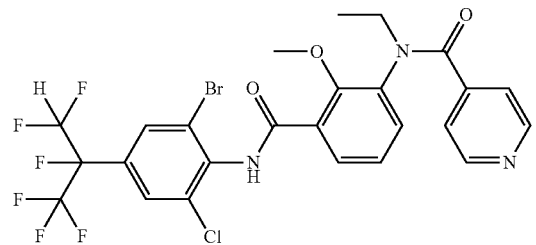 [SMILES: CCN(C(=O)c1ccncc1)c1cccc(C(=O)Nc2c(Cl)cc(C(F)(C(F)F)C(F)(F)F)cc2Br)c1OC]

A solution of N-[3-[[2-bromo-4-[1-[bromo(difluoro)methyl]-1,2,2,2-tetrafluoro-ethyl]-6-chloro-phenyl]carbamoyl]-2-methoxy-phenyl]-N-ethyl-pyridine-4-carboxamide (115 mg, 0.16 mmol, prepared analogously to the methods described above, entry 2, table B) dissolved in toluene (3 mL) was degassed with nitrogen, and then treated with tris(trimethylsilyl)silane (61 mg, 0.2404 mmol) and azo-bis-(isobutyronitrilE, AIBN) (61 mg, 0.016 mmol). The reaction stirred at room temperature for 23 h after which time LCMS showed reaction completion. The reaction mixture was quenched with 5 mL water and extracted with 3×10 mL ethylacetate. The combined organic layers were washed with 10 mL HCl-solution (2 mol.) and afterwards with 20 mL NaCl-solution, dried over Na$_2$SO$_4$, filtered and concentrated in vacuo. The crude product was purified by reversed phase chromatography to give the title product as a yellow resin. LCMS: (OA_Standard): 638, 640, 642 (M+H), retention time 1.03 min. $^1$H NMR (400 MHz, CHLOROFORM-d) δ ppm 1.44 (t, J=7.15 Hz, 3H); 3.73 (m, 1H); 3.96 (s, 3H); 4.26 (m, 1H); 5.99-6.41 (m, 1H); 7.25 (br, 1H); 7.32 (d, J=5.50 Hz, 2H); 7.51 (d, J=6.97 Hz, 1H); 7.62-7.70 (m, 1H); 7.78 (s, 1H); 7.96-8.11 (m, 1H) 8.49 (br s, 2H) 8.68 (br. s., 1H).

LC-MS Method: ZCQ13
ZQ Mass Spectrometer from Waters (Single Quadrupole Mass Spectrometer)
Instrument Parameter:
  Ionization method: Electrospray
  Polarity: positive and negative ions
  Capillary: 3.00 kV
  Cone: 30 V Extractor: 2.00 V
Source Temperature: 150° C.,
Desolvation Temperature: 350 C
Cone Gas Flow: 50 L/Hr
Desolvation Gas Flow: 400 L/Hr
Mass range: 100 to 900 Da
Acquity UPLC from Waters:
Binary pump, heated column compartment and diode-array detector.
Solvent degasser, binary pump, heated column compartment and diode-array detector.
Column: Waters UPLC HSS T3, 1.8 μm, 30×2.1 mm, Temp: 60° C.
DAD Wavelength range (nm): 210 to 500
Solvent Gradient:
A=H2O+5% MeOH+0.05% HCOOH
B=Acetonitril+0.05% HCOOH

| Time | A % | B % | Flow (ml/min) |
|---|---|---|---|
| 0.00 | 90 | 10 | 0.85 |
| 1.20 | 0 | 100.0 | 0.85 |
| 1.50 | 0 | 100.0 | 0.85 |

LC-MS Method: ZDQ13
ZQ Mass Spectrometer from Waters (Single Quadrupole Mass Spectrometer)
Instrument Parameter:
Ionization method: Electrospray
Polarity: positive and negative ions
Capillary: 3.00 kV
Cone: 30 V
Extractor: 2.00 V
Source Temperature: 150° C.,
Desolvation Temperature: 350 C
Cone Gas Flow: 50 L/Hr
Desolvation Gas Flow: 400 L/Hr
Mass range: 100 to 900 Da
Acquity UPLC from Waters:
Binary pump, heated column compartment and diode-array detector.
Solvent degasser, binary pump, heated column compartment and diode-array detector.
Column: Waters UPLC HSS T3, 1.8 μm, 30×2.1 mm, Temp: 60° C.
DAD Wavelength range (nm): 210 to 500
Solvent Gradient:
A=H2O+5% MeOH+0.05% HCOOH
B=Acetonitril+0.05% HCOOH

| Time | A % | B % | Flow (ml/min) |
|---|---|---|---|
| 0.00 | 90 | 10 | 0.85 |
| 1.20 | 0 | 100.0 | 0.85 |
| 1.50 | 0 | 100.0 | 0.85 |

LC-MS Method: OA_STANDARD
ZQ Mass Spectrometer from Waters (Single Quadrupole Mass Spectrometer)
Instrument Parameter:
Ionization method: Electrospray
Polarity: positive and negative ions
Capillary: 3.00 kV
Cone: 30 V
Extractor: 2.00 V
Source Temperature: 150° C.,
Desolvation Temperature: 350 C
Cone Gas Flow: 50 L/Hr
Desolvation Gas Flow: 400 L/Hr
Mass range: 100 to 900 Da
Acquity UPLC from Waters:
Binary pump, heated column compartment and diode-array detector.
Solvent degasser, binary pump, heated column compartment and diode-array detector.
Column: Waters UPLC HSS T3, 1.8 μm, 30×2.1 mm, Temp: 60° C.
DAD Wavelength range (nm): 210 to 500
Solvent Gradient:
A=H2O+5% MeOH+0.05% HCOOH
B=Acetonitril+0.05% HCOOH

| Time | A % | B % | Flow (ml/min) |
|---|---|---|---|
| 0.00 | 90 | 10 | 0.85 |
| 1.20 | 0 | 100.0 | 0.85 |
| 1.50 | 0 | 100.0 | 0.85 |

The following compounds illustrate the invention:

TABLE A

Radicals of formula (I)

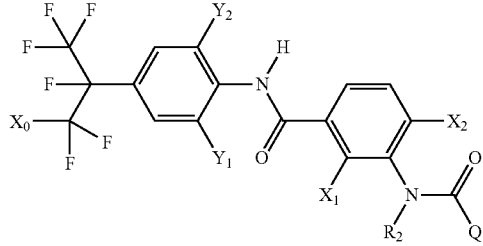

(I)

Wherein:

| Line | X1 | X2 | Q |
|---|---|---|---|
| 1 | F | H | 4-Pyridyl |
| 2 | OCH3 | H | 4-Pyridyl |
| 3 | H | H | 4-Pyridyl |
| 4 | F | CN | 4-Pyridyl |
| 5 | OCH3 | CN | 4-Pyridyl |
| 6 | H | CN | 4-Pyridyl |
| 7 | F | H | 3-Pyridyl |
| 8 | OCH3 | H | 3-Pyridyl |
| 9 | H | H | 3-Pyridyl |
| 10 | F | CN | 3-Pyridyl |
| 11 | OCH3 | CN | 3-Pyridyl |
| 12 | H | CN | 3-Pyridyl |
| 13 | F | H | 4-Cyanophenyl |
| 14 | OCH3 | H | 4-Cyanophenyl |
| 15 | H | H | 4-Cyanophenyl |
| 16 | F | CN | 4-Cyanophenyl |
| 17 | OCH3 | CN | 4-Cyanophenyl |
| 18 | H | CN | 4-Cyanophenyl |
| 19 | F | H | 4-Pyridyl-N-Oxide |
| 20 | OCH3 | H | 4-Pyridyl-N-Oxide |
| 21 | H | H | 4-Pyridyl-N-Oxide |
| 22 | F | CN | 4-Pyridyl-N-Oxide |
| 23 | OCH3 | CN | 4-Pyridyl-N-Oxide |
| 24 | H | CN | 4-Pyridyl-N-Oxide |
| 25 | F | H | 3-Pyridyl-N-Oxide |
| 26 | OCH3 | H | 3-Pyridyl-N-Oxide |
| 27 | H | H | 3-Pyridyl-N-Oxide |
| 28 | F | CN | 3-Pyridyl-N-Oxide |

TABLE A-continued

Radicals of formula (I)

(I)

Wherein:

| Line | X1 | X2 | Q |
|---|---|---|---|
| 29 | OCH3 | CN | 3-Pyridyl-N-Oxide |
| 30 | H | CN | 3-Pyridyl-N-Oxide |
| 31 | F | H | 4-Cyano-2-methylphenyl |
| 32 | OCH3 | H | 4-Cyano-2-methylphenyl |
| 33 | H | H | 4-Cyano-2-methylphenyl |
| 34 | F | CN | 4-Cyano-2-methylphenyl |
| 35 | OCH3 | CN | 4-Cyano-2-methylphenyl |
| 36 | H | CN | 4-Cyano-2-methylphenyl |

Table 1 provides 36 compounds of formula (I) wherein X0 is H, Y1 is Cl, Y2 is Cl, R2 is H, and X1, X2 and Q are as defined in Table A, lines 1-36.

Table 2 provides 36 compounds of formula (I) wherein X0 is Cl, Y1 is Cl, Y2 is Cl, R2 is H, and X1, X2 and Q are as defined in Table A, lines 1-36.

Table 3 provides 36 compounds of formula (I) wherein X0 is Br, Y1 is Cl, Y2 is Cl, R2 is H, and X1, X2 and Q are as defined in Table A, lines 1-36.

Table 4 provides 36 compounds of formula (I) wherein X0 is H, Y1 is Br, Y2 is Cl, R2 is H, and X1, X2 and Q are as defined in Table A lines 1-36.

Table 5 provides 36 compounds of formula (I) wherein X0 is Cl, Y1 is Br, Y2 is Cl, R2 is H, and X1, X2 and Q are as defined in Table A, lines 1-36.

Table 6 provides 36 compounds of formula (I) wherein X0 is Br, Y1 is Br, Y2 is Cl, R2 is H, and X1, X2 and Q are as defined in Table A lines 1-36.

Table 7 provides 36 compounds of formula (I) wherein X0 is H, Y1 is Me, Y2 is Cl, R2 is H, and X1, X2 and Q are as defined in Table A, lines 1-36.

Table 8 provides 36 compounds of formula (I) wherein X0 is Cl, Y1 is Me, Y2 is Cl, R2 is H, and X1, X2 and Q are as defined in Table A, lines 1-36.

Table 9 provides 36 compounds of formula (I) wherein X0 is Br, Y1 is Me, Y2 is Cl, R2 is H, and X1, X2 and Q are as defined in Table A, lines 1-36.

Table 10 provides 36 compounds of formula (I) wherein X0 is H, Y1 is Et, Y2 is Cl, R2 is H, and X1, X2 and Q are as defined in Table A, lines 1-36.

Table 11 provides 36 compounds of formula (I) wherein X0 is Cl, Y1 is Et, Y2 is Cl, R2 is H, and X1, X2 and Q are as defined in Table A, lines 1-36.

Table 12 provides 36 compounds of formula (I) wherein X0 is Br, Y1 is Et, Y2 is Cl, R2 is H, and X1, X2 and Q are as defined in Table A, lines 1-36.

Table 13 provides 36 compounds of formula (I) wherein X0 is H, Y1 is OCHF2, Y2 is Cl, R2 is H, and X1, X2 and Q are as defined in Table A, lines 1-36.

Table 14 provides 36 compounds of formula (I) wherein X0 is Cl, Y1 is OCHF2, Y2 is Cl, R2 is H, and X1, X2 and Q are as defined in Table A, lines 1-36.

Table 15 provides 36 compounds of formula (I) wherein X0 is Br, Y1 is OCHF2, Y2 is Cl, R2 is H, and X1, X2 and Q are as defined in Table A, lines 1-36.

Table 16 provides 36 compounds of formula (I) wherein X0 is H, Y1 is Br, Y2 is Br, R2 is H, and X1, X2 and Q are as defined in Table A, lines 1-36.

Table 17 provides 36 compounds of formula (I) wherein X0 is Cl, Y1 is Br, Y2 is Br, R2 is H, and X1, X2 and Q are as defined in Table A lines 1-36.

Table 18 provides 36 compounds of formula (I) wherein X0 is Br, Y1 is Br, Y2 is Br, R2 is H, and X1, X2 and Q are as defined in Table A, lines 1-36.

Table 19 provides 36 compounds of formula (I) wherein X0 is H, Y1 is Et, Y2 is Br, R2 is H, and X1, X2 and Q are as defined in Table A, lines 1-36.

Table 20 provides 36 compounds of formula (I) wherein X0 is Cl, Y1 is Et, Y2 is Br, R2 is H, and X1, X2 and Q are as defined in Table A, lines 1-36.

Table 21 provides 36 compounds of formula (I) wherein X0 is Br, Y1 is Et, Y2 is Br, R2 is H, and X1, X2 and Q are as defined in Table A, lines 1-36.

Table 22 provides 36 compounds of formula (I) wherein X0 is H, Y1 is OCHF2, Y2 is Br, R2 is H, and X1, X2 and Q are as defined in Table A lines 1-36.

Table 23 provides 36 compounds of formula (I) wherein X0 is Cl, Y1 is OCHF2, Y2 is Br, R2 is H, and X1, X2 and Q are as defined in Table A lines 1-36.

Table 24 provides 36 compounds of formula (I) wherein X0 is Br, Y1 is OCHF2, Y2 is Br, R2 is H, and X1, X2 and Q are as defined in Table A, lines 1-30 lines 1-36.

Table 25 provides 36 compounds of formula (I) wherein X0 is H, Y1 is Br, Y2 is Me, R2 is H, and X1, X2 and Q are as defined in Table A, lines 1-36.

Table 26 provides 36 compounds of formula (I) wherein X0 is Cl, Y1 is Br, Y2 is Me, R2 is H, and X1, X2 and Q are as defined in Table A lines 1-36.

Table 27 provides 36 compounds of formula (I) wherein X0 is Br, Y1 is Br, Y2 is Me, R2 is H, and X1, X2 and Q are as defined in Table A, lines 1-36.

Table 28 provides 36 compounds of formula (I) wherein X0 is H, Y1 is Me, Y2 is Me, R2 is H, and X1, X2 and Q are as defined in Table A, lines 1-36.

Table 29 provides 36 compounds of formula (I) wherein X0 is Cl, Y1 is Me, Y2 is Me, R2 is H, and X1, X2 and Q are as defined in Table A, lines 1-36.

Table 30 provides 36 compounds of formula (I) wherein X0 is Br, Y1 is Me, Y2 is Me, R2 is H, and X1, X2 and Q are as defined in Table A, lines 1-36.

Table 31 provides 36 compounds of formula (I) wherein X0 is H, Y1 is Et, Y2 is Me, R2 is H, and X1, X2 and Q are as defined in Table A, lines 1-36.

Table 32 provides 36 compounds of formula (I) wherein X0 is Cl, Y1 is Et, Y2 is Me, R2 is H, and X1, X2 and Q are as defined in Table A, lines 1-36.

Table 33 provides 36 compounds of formula (I) wherein X0 is Br, Y1 is Et, Y2 is Me, R2 is H, and X1, X2 and Q are as defined in Table A, lines 1-36.

Table 34 provides 36 compounds of formula (I) wherein X0 is H, Y1 is OCHF2, Y2 is Me, R2 is H, and X1, X2 and Q are as defined in Table A, lines 1-36.

Table 35 provides 36 compounds of formula (I) wherein X0 is Cl, Y1 is OCHF2, Y2 is Me, R2 is H, and X1, X2 and Q are as defined in Table A, lines 1-36.

Table 36 provides 36 compounds of formula (I) wherein X0 is Br, Y1 is OCHF2, Y2 is Me, R2 is H, and X1, X2 and Q are as defined in Table A lines 1-36.

Table 37 provides 36 compounds of formula (I) wherein X0 is H, Y1 is Et, Y2 is Et, R2 is H, and X1, X2 and Q are as defined in Table A, lines 1-36.

Table 38 provides 36 compounds of formula (I) wherein X0 is Cl, Y1 is Et, Y2 is Et, R2 is H, and X1, X2 and Q are as defined in Table A, lines 1-36.

Table 39 provides 36 compounds of formula (I) wherein X0 is Br, Y1 is Et, Y2 is Et, R2 is H, and X1, X2 and Q are as defined in Table A, lines 1-36.

Table 40 provides 36 compounds of formula (I) wherein X0 is H, Y1 is OCHF2, Y2 is Et, R2 is H, and X1, X2 and Q are as defined in Table A, lines 1-36.

Table 41 provides 36 compounds of formula (I) wherein X0 is Cl, Y1 is OCHF2, Y2 is Et, R2 is H, and X1, X2 and Q are as defined in Table A, lines 1-36.

Table 42 provides 36 compounds of formula (I) wherein X0 is Br, Y1 is OCHF2, Y2 is Et, R2 is H, and X1, X2 and Q are as defined in Table A, lines 1-36.

Table 43 provides 36 compounds of formula (I) wherein X0 is H, Y1 is Cl, Y2 is Cl, R2 is Me, and X1, X2 and Q are as defined in Table A, lines 1-36.

Table 44 provides 36 compounds of formula (I) wherein X0 is Cl, Y1 is Cl, Y2 is Cl, R2 is Me, and X1, X2 and Q are as defined in Table A, lines 1-36.

Table 45 provides 36 compounds of formula (I) wherein X0 is Br, Y1 is Cl, Y2 is Cl, R2 is Me, and X1, X2 and Q are as defined in Table A, lines 1-36.

Table 46 provides 36 compounds of formula (I) wherein X0 is H, Y1 is Br, Y2 is Cl, R2 is Me, and X1, X2 and Q are as defined in Table A, lines 1-36.

Table 47 provides 36 compounds of formula (I) wherein X0 is Cl, Y1 is Br, Y2 is Cl, R2 is Me, and X1, X2 and Q are as defined in Table A, lines 1-36.

Table 48 provides 36 compounds of formula (I) wherein X0 is Br, Y1 is Br, Y2 is Cl, R2 is Me, and X1, X2 and Q are as defined in Table A, lines 1-36.

Table 49 provides 36 compounds of formula (I) wherein X0 is H, Y1 is Me, Y2 is Cl, R2 is Me, and X1, X2 and Q are as defined in Table A, lines 1-36.

Table 50 provides 36 compounds of formula (I) wherein X0 is Cl, Y1 is Me, Y2 is Cl, R2 is Me, and X1, X2 and Q are as defined in Table A, lines 1-36.

Table 51 provides 36 compounds of formula (I) wherein X0 is Br, Y1 is Me, Y2 is Cl, R2 is Me, and X1, X2 and Q are as defined in Table A, lines 1-36.

Table 52 provides 36 compounds of formula (I) wherein X0 is H, Y1 is Et, Y2 is Cl, R2 is Me, and X1, X2 and Q are as defined in Table A, lines 1-36.

Table 53 provides 36 compounds of formula (I) wherein X0 is Cl, Y1 is Et, Y2 is Cl, R2 is Me, and X1, X2 and Q are as defined in Table A, lines 1-36.

Table 54 provides 36 compounds of formula (I) wherein X0 is Br, Y1 is Et, Y2 is Cl, R2 is Me, and X1, X2 and Q are as defined in Table A, lines 1-36.

Table 55 provides 36 compounds of formula (I) wherein X0 is H, Y1 is OCHF2, Y2 is Cl, R2 is Me, and X1, X2 and Q are as defined in Table A, lines 1-36.

Table 56 provides 36 compounds of formula (I) wherein X0 is Cl, Y1 is OCHF2, Y2 is Cl, R2 is Me, and X1, X2 and Q are as defined in Table A, lines 1-36.

Table 57 provides 36 compounds of formula (I) wherein X0 is Br, Y1 is OCHF2, Y2 is Cl, R2 is Me, and X1, X2 and Q are as defined in Table A, lines 1-36.

Table 58 provides 36 compounds of formula (I) wherein X0 is H, Y1 is Br, Y2 is Br, R2 is Me, and X1, X2 and Q are as defined in Table A, lines 1-36.

Table 59 provides 36 compounds of formula (I) wherein X0 is Cl, Y1 is Br, Y2 is Br, R2 is Me, and X1, X2 and Q are as defined in Table A, lines 1-36.

Table 60 provides 36 compounds of formula (I) wherein X0 is Br, Y1 is Br, Y2 is Br, R2 is Me, and X1, X2 and Q are as defined in Table A, lines 1-36.

Table 61 provides 36 compounds of formula (I) wherein X0 is H, Y1 is Et, Y2 is Br, R2 is Me, and X1, X2 and Q are as defined in Table A, lines 1-36.

Table 62 provides 36 compounds of formula (I) wherein X0 is Cl, Y1 is Et, Y2 is Br, R2 is Me, and X1, X2 and Q are as defined in Table A, lines 1-36.

Table 63 provides 36 compounds of formula (I) wherein X0 is Br, Y1 is Et, Y2 is Br, R2 is Me, and X1, X2 and Q are as defined in Table A, lines 1-36.

Table 64 provides 36 compounds of formula (I) wherein X0 is H, Y1 is OCHF2, Y2 is Br, R2 is Me, and X1, X2 and Q are as defined in Table A, lines 1-36.

Table 65 provides 36 compounds of formula (I) wherein X0 is Cl, Y1 is OCHF2, Y2 is Br, R2 is Me, and X1, X2 and Q are as defined in Table A, lines 1-36.

Table 66 provides 36 compounds of formula (I) wherein X0 is Br, Y1 is OCHF2, Y2 is Br, R2 is Me, and X1, X2 and Q are as defined in Table A, lines 1-36.

Table 67 provides 36 compounds of formula (I) wherein X0 is H, Y1 is Br, Y2 is Me, R2 is Me, and X1, X2 and Q are as defined in Table A, lines 1-36.

Table 68 provides 36 compounds of formula (I) wherein X0 is Cl, Y1 is Br, Y2 is Me, R2 is Me, and X1, X2 and Q are as defined in Table A, lines 1-36.

Table 69 provides 36 compounds of formula (I) wherein X0 is Br, Y1 is Br, Y2 is Me, R2 is Me, and X1, X2 and Q are as defined in Table A, lines 1-36.

Table 70 provides 36 compounds of formula (I) wherein X0 is H, Y1 is Me, Y2 is Me, R2 is Me, and X1, X2 and Q are as defined in Table A, lines 1-36.

Table 71 provides 36 compounds of formula (I) wherein X0 is Cl, Y1 is Me, Y2 is Me, R2 is Me, and X1, X2 and Q are as defined in Table A, lines 1-36.

Table 72 provides 36 compounds of formula (I) wherein X0 is Br, Y1 is Me, Y2 is Me, R2 is Me, and X1, X2 and Q are as defined in Table A, lines 1-36.

Table 73 provides 36 compounds of formula (I) wherein X0 is H, Y1 is Et, Y2 is Me, R2 is Me, and X1, X2 and Q are as defined in Table A, lines 1-36.

Table 74 provides 36 compounds of formula (I) wherein X0 is Cl, Y1 is Et, Y2 is Me, R2 is Me, and X1, X2 and Q are as defined in Table A, lines 1-36.

Table 75 provides 36 compounds of formula (I) wherein X0 is Br, Y1 is Et, Y2 is Me, R2 is Me, and X1, X2 and Q are as defined in Table A, lines 1-36.

Table 76 provides 36 compounds of formula (I) wherein X0 is H, Y1 is OCHF2, Y2 is Me, R2 is Me, and X1, X2 and Q are as defined in Table A, lines 1-36.

Table 77 provides 36 compounds of formula (I) wherein X0 is Cl, Y1 is OCHF2, Y2 is Me, R2 is Me, and X1, X2 and Q are as defined in Table A, lines 1-36.

Table 78 provides 36 compounds of formula (I) wherein X0 is Br, Y1 is OCHF2, Y2 is Me, R2 is Me, and X1, X2 and Q are as defined in Table A, lines 1-36.

Table 79 provides 36 compounds of formula (I) wherein X0 is H, Y1 is Et, Y2 is Et, R2 is Me, and X1, X2 and Q are as defined in Table A, lines 1-36.

Table 80 provides 36 compounds of formula (I) wherein X0 is Cl, Y1 is Et, Y2 is Et, R2 is Me, and X1, X2 and Q are as defined in Table A, lines 1-36.

Table 81 provides 36 compounds of formula (I) wherein X0 is Br, Y1 is Et, Y2 is Et, R2 is Me, and X1, X2 and Q are as defined in Table A, lines 1-36.

Table 82 provides 36 compounds of formula (I) wherein X0 is H, Y1 is OCHF2, Y2 is Et, R2 is Me, and X1, X2 and Q are as defined in Table A, lines 1-36.

Table 83 provides 36 compounds of formula (I) wherein X0 is Cl, Y1 is OCHF2, Y2 is Et, R2 is Me, and X1, X2 and Q are as defined in Table A, lines 1-36.

Table 84 provides 36 compounds of formula (I) wherein X0 is Br, Y1 is OCHF2, Y2 is Et, R2 is Me, and X1, X2 and Q are as defined in Table A, lines 1-36.

Table 85 provides 36 compounds of formula (I) wherein X0 is H, Y1 is Cl, Y2 is Cl, R2 is Et, and X1, X2 and Q are as defined in Table A, lines 1-36.

Table 86 provides 36 compounds of formula (I) wherein X0 is Cl, Y1 is Cl, Y2 is Cl, R2 is Et, and X1, X2 and Q are as defined in Table A, lines 1-36.

Table 87 provides 36 compounds of formula (I) wherein X0 is Br, Y1 is Cl, Y2 is Cl, R2 is Et, and X1, X2 and Q are as defined in Table A, lines 1-36.

Table 88 provides 36 compounds of formula (I) wherein X0 is H, Y1 is Br, Y2 is Cl, R2 is Et, and X1, X2 and Q are as defined in Table A, lines 1-36.

Table 89 provides 36 compounds of formula (I) wherein X0 is Cl, Y1 is Br, Y2 is Cl, R2 is Et, and X1, X2 and Q are as defined in Table A, lines 1-36.

Table 90 provides 36 compounds of formula (I) wherein X0 is Br, Y1 is Br, Y2 is Cl, R2 is Et, and X1, X2 and Q are as defined in Table A, lines 1-36.

Table 91 provides 36 compounds of formula (I) wherein X0 is H, Y1 is Me, Y2 is Cl, R2 is Et, and X1, X2 and Q are as defined in Table A, lines 1-36.

Table 92 provides 36 compounds of formula (I) wherein X0 is Cl, Y1 is Me, Y2 is Cl, R2 is Et, and X1, X2 and Q are as defined in Table A, lines 1-36.

Table 93 provides 36 compounds of formula (I) wherein X0 is Br, Y1 is Me, Y2 is Cl, R2 is Et, and X1, X2 and Q are as defined in Table A, lines 1-36.

Table 94 provides 36 compounds of formula (I) wherein X0 is H, Y1 is Et, Y2 is Cl, R2 is Et, and X1, X2 and Q are as defined in Table A, lines 1-36.

Table 95 provides 36 compounds of formula (I) wherein X0 is Cl, Y1 is Et, Y2 is Cl, R2 is Et, and X1, X2 and Q are as defined in Table A, lines 1-36.

Table 96 provides 36 compounds of formula (I) wherein X0 is Br, Y1 is Et, Y2 is Cl, R2 is Et, and X1, X2 and Q are as defined in Table A, lines 1-36.

Table 97 provides 36 compounds of formula (I) wherein X0 is H, Y1 is OCHF2, Y2 is Cl, R2 is Et, and X1, X2 and Q are as defined in Table A, lines 1-36.

Table 98 provides 36 compounds of formula (I) wherein X0 is Cl, Y1 is OCHF2, Y2 is Cl, R2 is Et, and X1, X2 and Q are as defined in Table A, lines 1-36.

Table 99 provides 36 compounds of formula (I) wherein X0 is Br, Y1 is OCHF2, Y2 is Cl, R2 is Et, and X1, X2 and Q are as defined in Table A, lines 1-36.

Table 100 provides 36 compounds of formula (I) wherein X0 is H, Y1 is Br, Y2 is Br, R2 is Et, and X1, X2 and Q are as defined in Table A, lines 1-36.

Table 101 provides 36 compounds of formula (I) wherein X0 is Cl, Y1 is Br, Y2 is Br, R2 is Et, and X1, X2 and Q are as defined in Table A, lines 1-36.

Table 102 provides 36 compounds of formula (I) wherein X0 is Br, Y1 is Br, Y2 is Br, R2 is Et, and X1, X2 and Q are as defined in Table A, lines 1-36.

Table 103 provides 36 compounds of formula (I) wherein X0 is H, Y1 is Et, Y2 is Br, R2 is Et, and X1, X2 and Q are as defined in Table A, lines 1-36.

Table 104 provides 36 compounds of formula (I) wherein X0 is Cl, Y1 is Et, Y2 is Br, R2 is Et, and X1, X2 and Q are as defined in Table A, lines 1-36.

Table 105 provides 36 compounds of formula (I) wherein X0 is Br, Y1 is Et, Y2 is Br, R2 is Et, and X1, X2 and Q are as defined in Table A, lines 1-36.

Table 106 provides 36 compounds of formula (I) wherein X0 is H, Y1 is OCHF2, Y2 is Br, R2 is Et, and X1, X2 and Q are as defined in Table A, lines 1-36.

Table 107 provides 36 compounds of formula (I) wherein X0 is Cl, Y1 is OCHF2, Y2 is Br, R2 is Et, and X1, X2 and Q are as defined in Table A, lines 1-36.

Table 108 provides 36 compounds of formula (I) wherein X0 is Br, Y1 is OCHF2, Y2 is Br, R2 is Et, and X1, X2 and Q are as defined in Table A, lines 1-36.

Table 109 provides 36 compounds of formula (I) wherein X0 is H, Y1 is Br, Y2 is Me, R2 is Et, and X1, X2 and Q are as defined in Table A, lines 1-36.

Table 110 provides 36 compounds of formula (I) wherein X0 is Cl, Y1 is Br, Y2 is Me, R2 is Et, and X1, X2 and Q are as defined in Table A, lines 1-36.

Table 111 provides 36 compounds of formula (I) wherein X0 is Br, Y1 is Br, Y2 is Me, R2 is Et, and X1, X2 and Q are as defined in Table A, lines 1-36.

Table 112 provides 36 compounds of formula (I) wherein X0 is H, Y1 is Me, Y2 is Me, R2 is Et, and X1, X2 and Q are as defined in Table A, lines 1-36.

Table 113 provides 36 compounds of formula (I) wherein X0 is Cl, Y1 is Me, Y2 is Me, R2 is Et, and X1, X2 and Q are as defined in Table A, lines 1-36.

Table 114 provides 36 compounds of formula (I) wherein X0 is Br, Y1 is Me, Y2 is Me, R2 is Et, and X1, X2 and Q are as defined in Table A, lines 1-36.

Table 115 provides 36 compounds of formula (I) wherein X0 is H, Y1 is Et, Y2 is Me, R2 is Et, and X1, X2 and Q are as defined in Table A, lines 1-36.

Table 116 provides 36 compounds of formula (I) wherein X0 is Cl, Y1 is Et, Y2 is Me, R2 is Et, and X1, X2 and Q are as defined in Table A, lines 1-36.

Table 117 provides 36 compounds of formula (I) wherein X0 is Br, Y1 is Et, Y2 is Me, R2 is Et, and X1, X2 and Q are as defined in Table A, lines 1-36.

Table 118 provides 36 compounds of formula (I) wherein X0 is H, Y1 is OCHF2, Y2 is Me, R2 is Et, and X1, X2 and Q are as defined in A, lines 1-36.

Table 119 provides 36 compounds of formula (I) wherein X0 is Cl, Y1 is OCHF2, Y2 is Me, R2 is Et, and X1, X2 and Q are as defined in Table A, lines 1-36.

Table 120 provides 36 compounds of formula (I) wherein X0 is Br, Y1 is OCHF2, Y2 is Me, R2 is Et, and X1, X2 and Q are as defined in Table A, lines 1-36.

Table 121 provides 36 compounds of formula (I) wherein X0 is H, Y1 is Et, Y2 is Et, R2 is Et, and X1, X2 and Q are as defined in Table A, lines 1-36.

Table 122 provides 36 compounds of formula (I) wherein X0 is Cl, Y1 is Et, Y2 is Et, R2 is Et, and X1, X2 and Q are as defined in Table A, lines 1-36.

Table 123 provides 36 compounds of formula (I) wherein X0 is Br, Y1 is Et, Y2 is Et, R2 is Et, and X1, X2 and Q are as defined in Table A, lines 1-36.

Table 124 provides 36 compounds of formula (I) wherein X0 is H, Y1 is OCHF2, Y2 is Et, R2 is Et, and X1, X2 and Q are as defined in Table A, lines 1-36.

Table 125 provides 36 compounds of formula (I) wherein X0 is Cl, Y1 is OCHF2, Y2 is Et, R2 is Et, and X1, X2 and Q are as defined in Table A, lines 1-36.

Table 126 provides 36 compounds of formula (I) wherein X0 is Br, Y1 is OCHF2, Y2 is Et, R2 is Et, and X1, X2 and Q are as defined in Table A, lines 1-36.

TABLE B

Properties of Prepared Compounds

| Entry | STRUCTURE | RT (min) | [M + H] (measured) | Method | MP ° C. |
|---|---|---|---|---|---|
| 1 | 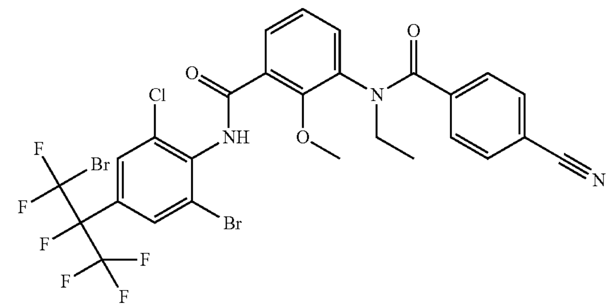 [SMILES: CCN(C(=O)c1ccc(C#N)cc1)c1cccc(C(=O)Nc2c(Cl)cc(C(F)(C(F)(F)F)C(F)(F)Br)cc2Br)c1OC] | 1.20 | 740, 742, 744 | ZDQ13 | |
| 2 | 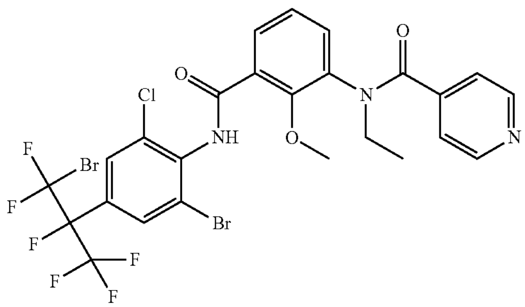 [SMILES: CCN(C(=O)c1ccncc1)c1cccc(C(=O)Nc2c(Cl)cc(C(F)(C(F)(F)F)C(F)(F)Br)cc2Br)c1OC] | 1.11 | 716, 718, 720 | ZDQ13 | |
| 3 | 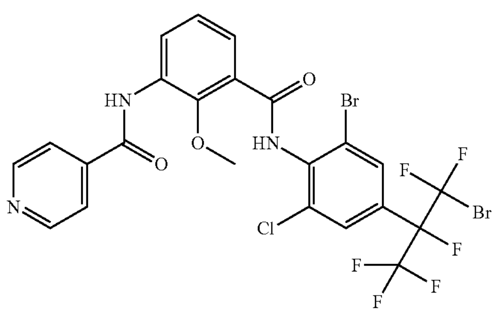 [SMILES: COc1c(NC(=O)c2ccncc2)cccc1C(=O)Nc1c(Cl)cc(C(F)(C(F)(F)F)C(F)(F)Br)cc1Br] | 1.10 | 688, 690, 692 | ZDQ13 | |
| 4 | 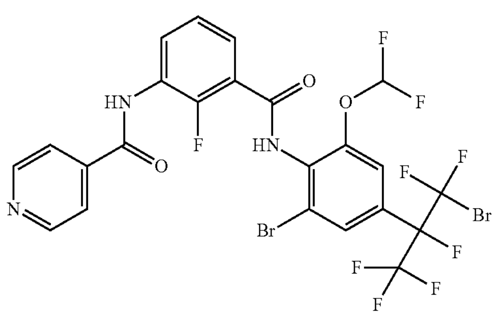 [SMILES: O=C(Nc1cccc(C(=O)Nc2c(Br)cc(C(F)(C(F)(F)F)C(F)(F)Br)cc2OC(F)F)c1F)c1ccncc1] | 1.07 | 708, 710, 712 | ZCQ13 | |

TABLE B-continued

Properties of Prepared Compounds

| Entry | STRUCTURE | RT (min) | [M + H] (measured) | Method | MP ° C. |
|---|---|---|---|---|---|
| 5 | 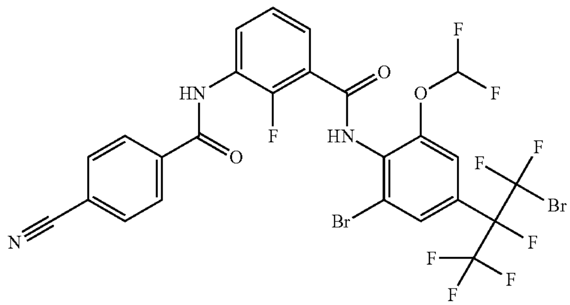 [SMILES: N#Cc1ccc(C(=O)Nc2cccc(C(=O)Nc3c(Br)cc(C(F)(C(F)(F)F)C(F)(F)Br)cc3OC(F)F)c2F)cc1] | 1.15 | 732, 734, 736 | ZCQ13 | |
| 6 | 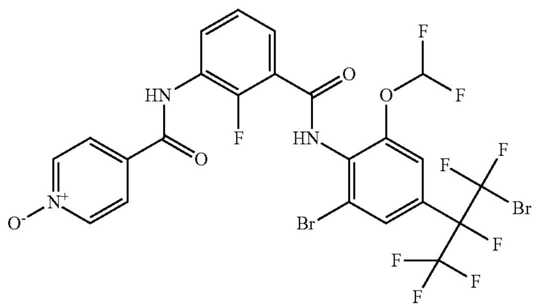 [SMILES: O=C(Nc1cccc(C(=O)Nc2c(Br)cc(C(F)(C(F)(F)F)C(F)(F)Br)cc2OC(F)F)c1F)c1cc[n+]([O-])cc1] | 1.00 | 724, 726, 728 | ZCQ13 | |
| 7 | 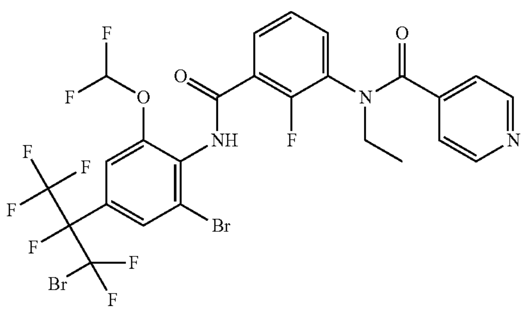 [SMILES: CCN(C(=O)c1ccncc1)c1cccc(C(=O)Nc2c(Br)cc(C(F)(C(F)(F)F)C(F)(F)Br)cc2OC(F)F)c1F] | 1.10 | 736, 738, 740 | | 162-164 |
| 8 | 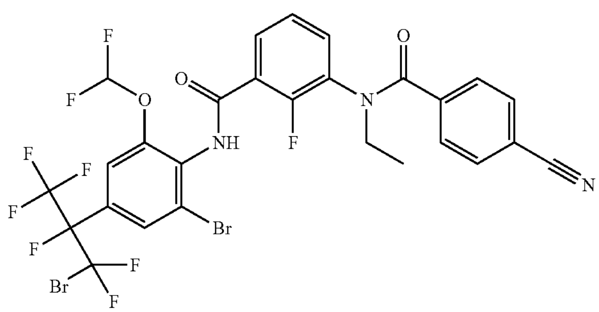 [SMILES: CCN(C(=O)c1ccc(C#N)cc1)c1cccc(C(=O)Nc2c(Br)cc(C(F)(C(F)(F)F)C(F)(F)Br)cc2OC(F)F)c1F] | 1.17 | 760, 762, 764 | ZCQ13 | |
| 9 | 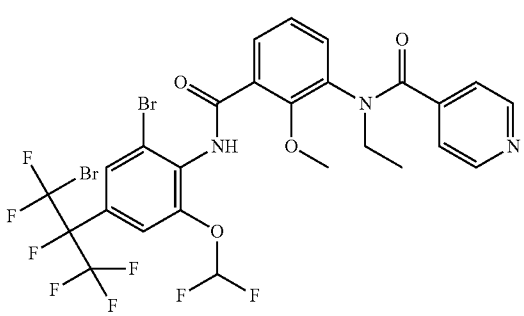 [SMILES: CCN(C(=O)c1ccncc1)c1cccc(C(=O)Nc2c(Br)cc(C(F)(C(F)(F)F)C(F)(F)Br)cc2OC(F)F)c1OC] | 1.11 | 748, 750, 752 | ZCQ13 | |

TABLE B-continued

Properties of Prepared Compounds

| Entry | STRUCTURE | RT (min) | [M + H] (measured) | Method | MP ° C. |
|---|---|---|---|---|---|
| 10 | 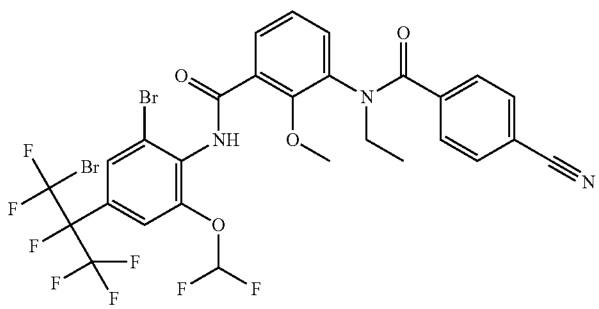 [SMILES: CCN(C(=O)c1ccc(C#N)cc1)c1cccc(C(=O)Nc2c(Br)cc(C(F)(C(F)(F)F)C(F)(F)Br)cc2OC(F)F)c1OC] | 1.18 | 772, 774, 776 | ZCQ13 | |
| 11 | 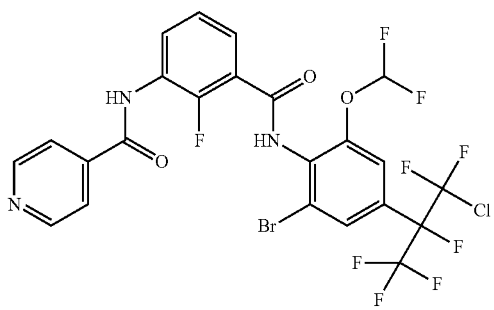 [SMILES: O=C(Nc1cccc(C(=O)Nc2c(Br)cc(C(F)(C(F)(F)F)C(F)(F)Cl)cc2OC(F)F)c1F)c1ccncc1] | 1.06 | 664, 666, 668 | ZCQ13 | 118-157 |
| 12 | 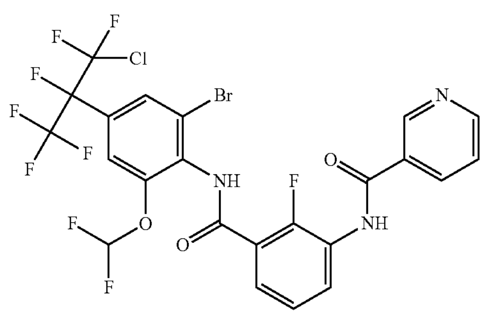 [SMILES: O=C(Nc1cccc(C(=O)Nc2c(Br)cc(C(F)(C(F)(F)F)C(F)(F)Cl)cc2OC(F)F)c1F)c1cccnc1] | 1.08 | 664, 666, 668 | ZCQ13 | 140-151 |
| 13 | 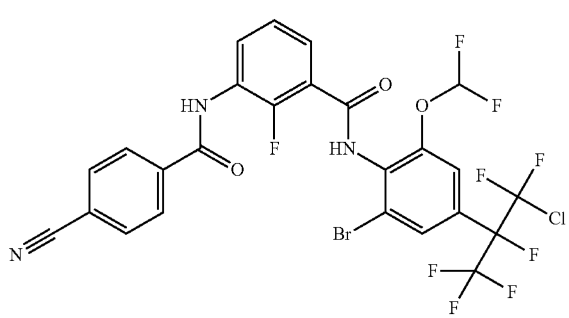 [SMILES: N#Cc1ccc(C(=O)Nc2cccc(C(=O)Nc3c(Br)cc(C(F)(C(F)(F)F)C(F)(F)Cl)cc3OC(F)F)c2F)cc1] | 1.15 | 688, 690, 692 | ZCQ13 | 116-151 |

TABLE B-continued

Properties of Prepared Compounds

| Entry | STRUCTURE | RT (min) | [M + H] (measured) | Method | MP ° C. |
|---|---|---|---|---|---|
| 14 | 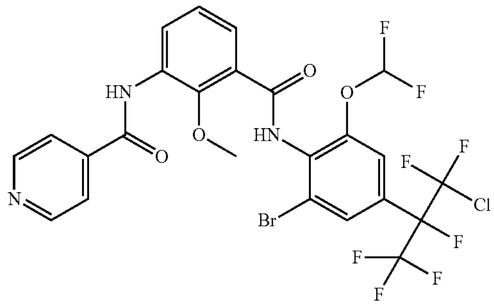 [SMILES: COc1c(NC(=O)c2ccncc2)cccc1C(=O)Nc1c(Br)cc(C(F)(C(F)(F)F)C(F)(F)Cl)cc1OC(F)F] | | | | 172-174 |
| 15 | 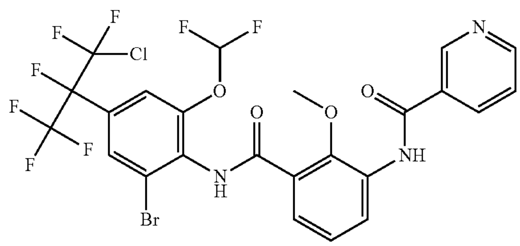 [SMILES: COc1c(NC(=O)c2cccnc2)cccc1C(=O)Nc1c(Br)cc(C(F)(C(F)(F)F)C(F)(F)Cl)cc1OC(F)F] | 1.10 | 676, 678, 680 | ZCQ13 | 90-170 |
| 16 | 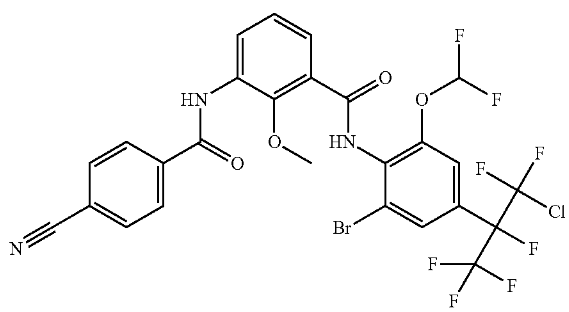 [SMILES: COc1c(NC(=O)c2ccc(C#N)cc2)cccc1C(=O)Nc1c(Br)cc(C(F)(C(F)(F)F)C(F)(F)Cl)cc1OC(F)F] | | | $^1$H NMR (400 MHz, CDCl$_3$, δ in ppm): 8.90 (s, 1H), 8.67 (d, J = 8.1 Hz, 1H), 8.46 (s, 1H), 8.03 (d, J = 9 Hz, 2H), 7.90-7.80 (m, 4H), 7.52 (s, 1H), 7.39 (t, J = 8.1 Hz, 1H), 6.63 (t, J = 73 Hz, 1H), 4.04 (s, 3H). | 97-172 |
| 17 | 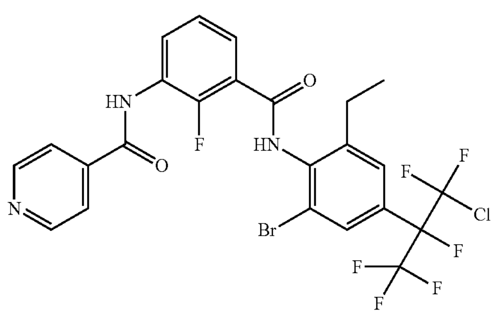 [SMILES: CCc1cc(C(F)(C(F)(F)F)C(F)(F)Cl)cc(Br)c1NC(=O)c1cccc(NC(=O)c2ccncc2)c1F] | 1.10 | 626, 628, 630 | ZCQ13 | 108-190 |
| 18 | 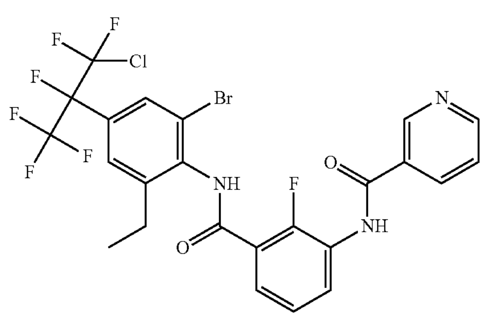 [SMILES: CCc1cc(C(F)(C(F)(F)F)C(F)(F)Cl)cc(Br)c1NC(=O)c1cccc(NC(=O)c2cccnc2)c1F] | | | | 171-173 |

TABLE B-continued

Properties of Prepared Compounds

| Entry | STRUCTURE | RT (min) | [M + H] (measured) | Method | MP °C. |
|---|---|---|---|---|---|
| 19 | 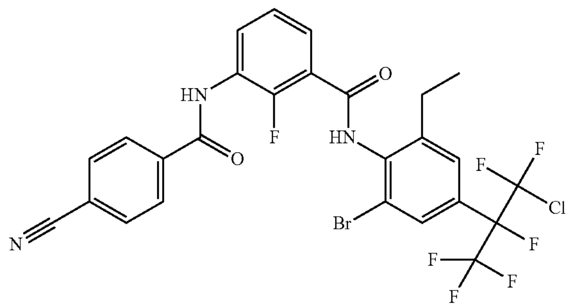 [SMILES: CCc1cc(C(F)(C(F)(F)F)C(F)(F)Cl)cc(Br)c1NC(=O)c1cccc(NC(=O)c2ccc(C#N)cc2)c1F] | 1.17 | 650, 652, 654 | ZCQ13 | 123-202 |
| 20 | 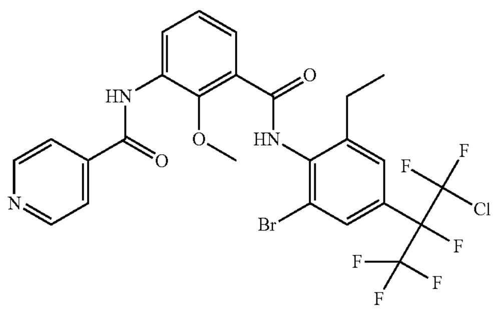 [SMILES: CCc1cc(C(F)(C(F)(F)F)C(F)(F)Cl)cc(Br)c1NC(=O)c1cccc(NC(=O)c2ccncc2)c1OC] | 1.12 | 638, 640, 642 | ZCQ13 | 99-162 |
| 21 | 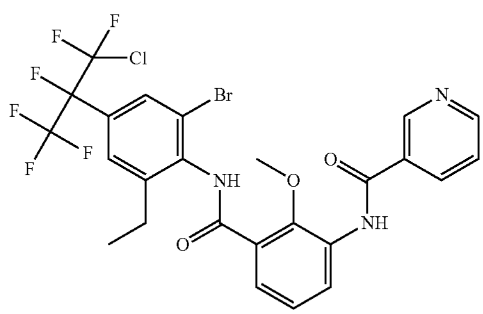 [SMILES: CCc1cc(C(F)(C(F)(F)F)C(F)(F)Cl)cc(Br)c1NC(=O)c1cccc(NC(=O)c2cccnc2)c1OC] | 1.12 | 638, 640, 642 | ZCQ13 | 87-168 |
| 22 | 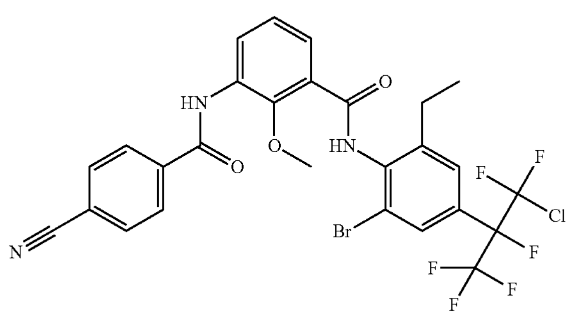 [SMILES: CCc1cc(C(F)(C(F)(F)F)C(F)(F)Cl)cc(Br)c1NC(=O)c1cccc(NC(=O)c2ccc(C#N)cc2)c1OC] | 1.19 | 662, 664, 666 | ZCQ13 | 110-170 |
| 23 | 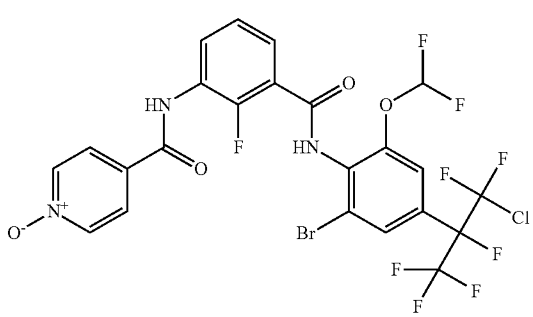 [SMILES: O=C(Nc1cccc(C(=O)Nc2c(Br)cc(C(F)(C(F)(F)F)C(F)(F)Cl)cc2OC(F)F)c1F)c1cc[n+]([O-])cc1] | | | | 230-232 |

TABLE B-continued

Properties of Prepared Compounds

| Entry | STRUCTURE | RT (min) | [M + H] (measured) | Method | MP ° C. |
|---|---|---|---|---|---|
| 24 | 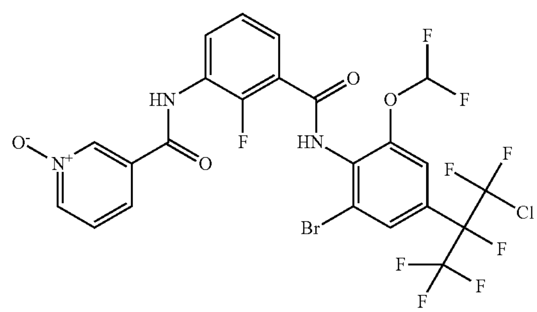 [SMILES: O=C(Nc1cccc(C(=O)Nc2c(Br)cc(C(F)(C(F)(F)F)C(F)(F)Cl)cc2OC(F)F)c1F)c1ccc[n+]([O-])c1] | | | | 197-201 |
| 25 | 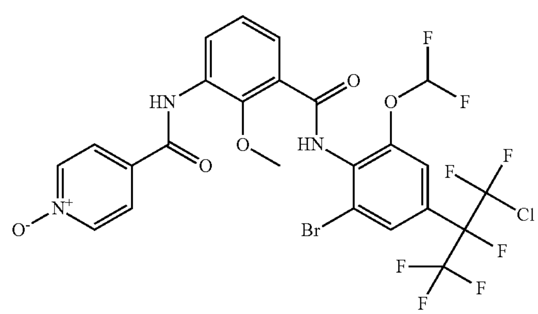 [SMILES: COc1c(NC(=O)c2cc[n+]([O-])cc2)cccc1C(=O)Nc1c(Br)cc(C(F)(C(F)(F)F)C(F)(F)Cl)cc1OC(F)F] | 1.02 | 692, 694, 696 | ZCQ13 | 177-186 |
| 26 | 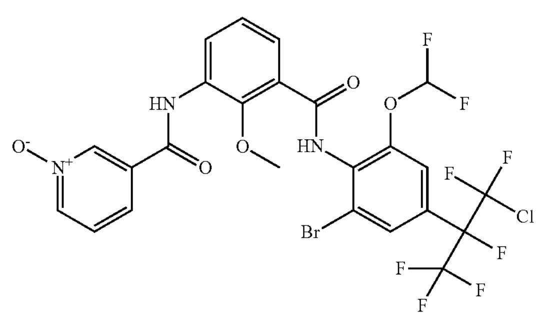 [SMILES: COc1c(NC(=O)c2ccc[n+]([O-])c2)cccc1C(=O)Nc1c(Br)cc(C(F)(C(F)(F)F)C(F)(F)Cl)cc1OC(F)F] | 1.02 | 692, 694, 696 | ZCQ13 | 172-179 |
| 27 | 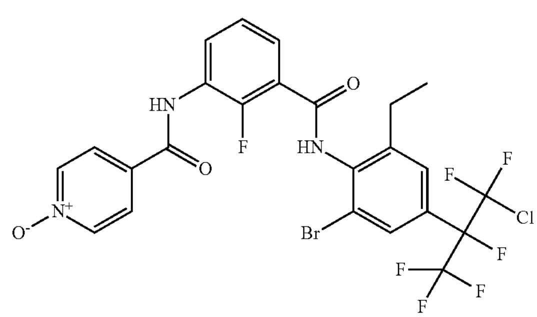 [SMILES: CCc1cc(C(F)(C(F)(F)F)C(F)(F)Cl)cc(Br)c1NC(=O)c1cccc(NC(=O)c2cc[n+]([O-])cc2)c1F] | 1.02 | 642, 644, 646 | ZCQ13 | 222-230 |

TABLE B-continued

Properties of Prepared Compounds

| Entry | STRUCTURE | RT (min) | [M + H] (measured) | Method | MP ° C. |
|---|---|---|---|---|---|
| 28 | 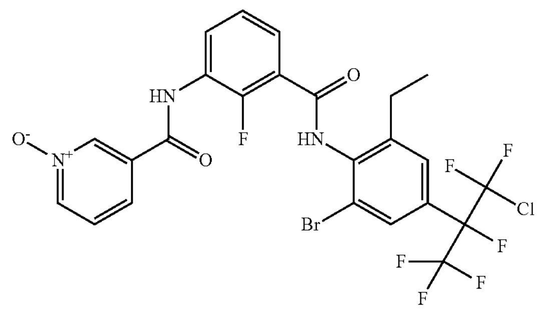 [SMILES: CCc1cc(C(F)(C(F)(F)F)C(F)(F)Cl)cc(Br)c1NC(=O)c1cccc(NC(=O)c2ccc[n+]([O-])c2)c1F] | | | | 237-239 |
| 29 | 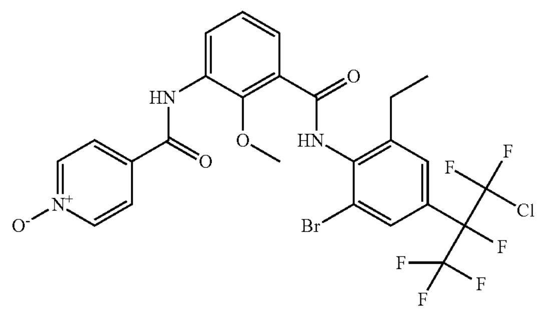 [SMILES: CCc1cc(C(F)(C(F)(F)F)C(F)(F)Cl)cc(Br)c1NC(=O)c1cccc(NC(=O)c2cc[n+]([O-])cc2)c1OC] | 1.04 | 654, 656, 658 | ZCQ13 | 158-167 |
| 30 | 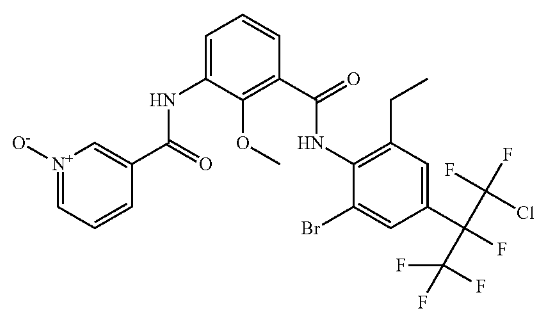 [SMILES: CCc1cc(C(F)(C(F)(F)F)C(F)(F)Cl)cc(Br)c1NC(=O)c1cccc(NC(=O)c2ccc[n+]([O-])c2)c1OC] | | | | 229-231 |
| 31 | 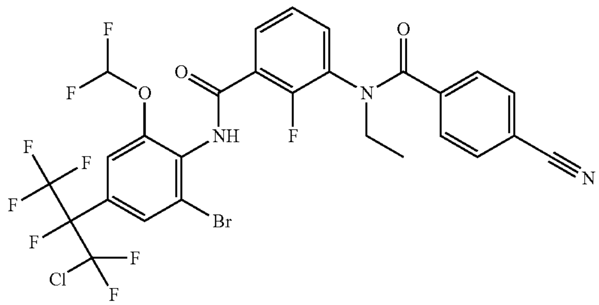 [SMILES: CCN(C(=O)c1ccc(C#N)cc1)c1cccc(C(=O)Nc2c(Br)cc(C(F)(C(F)(F)F)C(F)(F)Cl)cc2OC(F)F)c1F] | 1.17 | 716, 718, 720 | ZCQ13 | 80-150 |
| 32 | 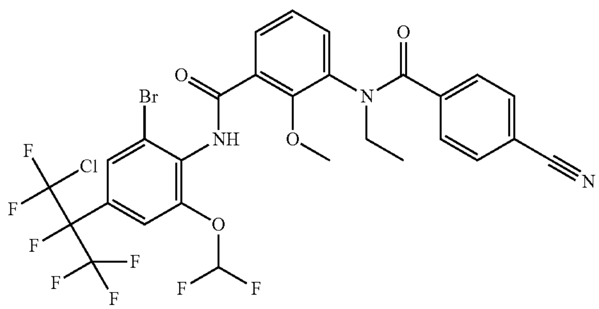 [SMILES: CCN(C(=O)c1ccc(C#N)cc1)c1cccc(C(=O)Nc2c(Br)cc(C(F)(C(F)(F)F)C(F)(F)Cl)cc2OC(F)F)c1OC] | 1.19 | 728, 730, 732 | ZCQ13 | 80-159 |

TABLE B-continued

Properties of Prepared Compounds

| Entry | STRUCTURE | RT (min) | [M + H] (measured) | Method | MP ° C. |
|---|---|---|---|---|---|
| 33 | 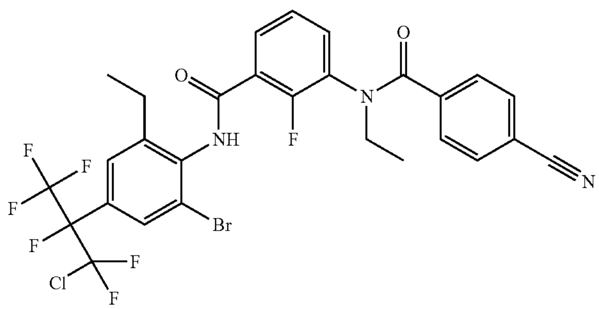 [SMILES: CCc1cc(C(F)(C(F)(F)F)C(F)(F)Cl)cc(Br)c1NC(=O)c1cccc(N(CC)C(=O)c2ccc(C#N)cc2)c1F] | 1.19 | 678, 680, 682 | ZCQ13 | 99-173 |
| 34 | 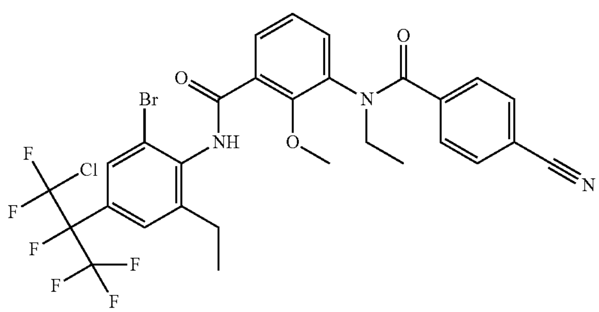 [SMILES: CCc1cc(C(F)(C(F)(F)F)C(F)(F)Cl)cc(Br)c1NC(=O)c1cccc(N(CC)C(=O)c2ccc(C#N)cc2)c1OC] | 1.22 | 690, 692, 694 | ZCQ13 | 106-152 |
| 35 | 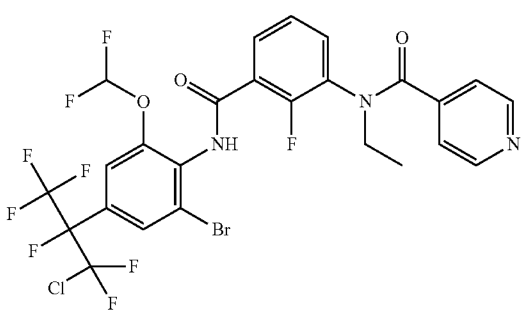 [SMILES: CCN(C(=O)c1ccncc1)c1cccc(C(=O)Nc2c(Br)cc(C(F)(C(F)(F)F)C(F)(F)Cl)cc2OC(F)F)c1F] | 1.10 | 692, 694, 696 | ZCQ13 | 106-154 |
| 36 | 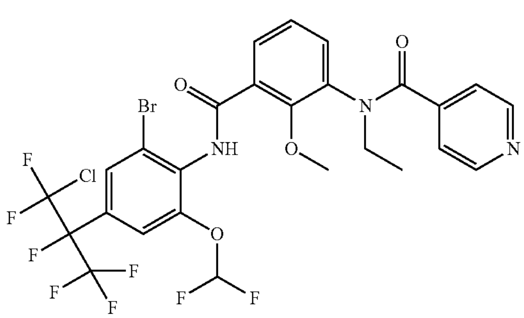 [SMILES: CCN(C(=O)c1ccncc1)c1cccc(C(=O)Nc2c(Br)cc(C(F)(C(F)(F)F)C(F)(F)Cl)cc2OC(F)F)c1OC] | 1.12 | 704, 706, 708 | ZCQ13 | 112-161 |

TABLE B-continued

Properties of Prepared Compounds

| Entry | STRUCTURE | RT (min) | [M + H] (measured) | Method | MP ° C. |
|---|---|---|---|---|---|
| 37 | 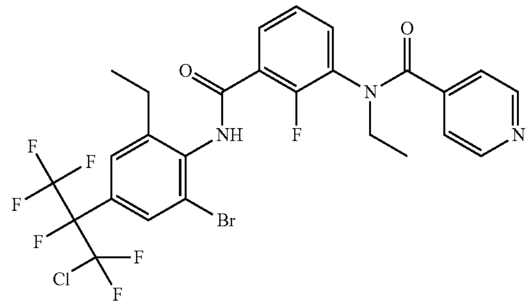 [SMILES: CCc1cc(C(F)(C(F)(F)F)C(F)(F)Cl)cc(Br)c1NC(=O)c1cccc(N(CC)C(=O)c2ccncc2)c1F] | 1.12 | 654, 656, 658 | ZCQ13 | 120-171 |
| 38 | 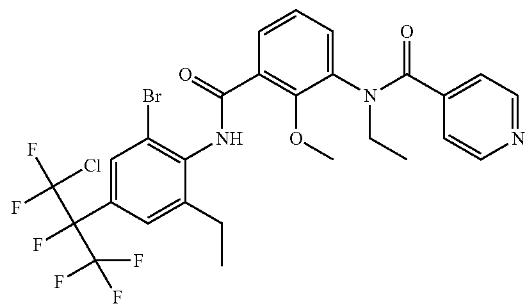 [SMILES: CCc1cc(C(F)(C(F)(F)F)C(F)(F)Cl)cc(Br)c1NC(=O)c1cccc(N(CC)C(=O)c2ccncc2)c1OC] | 1.14 | 666, 668, 670 | ZCQ13 | 90-155 |
| 39 | 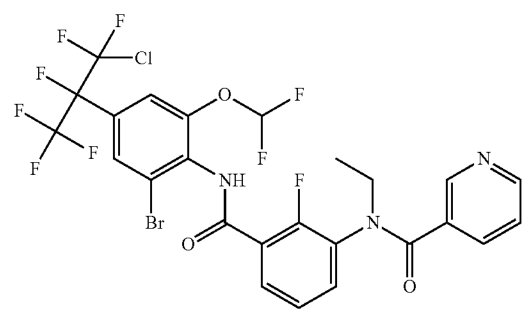 [SMILES: CCN(C(=O)c1cccnc1)c1cccc(C(=O)Nc2c(Br)cc(C(F)(C(F)(F)F)C(F)(F)Cl)cc2OC(F)F)c1F] | 1.11 | 692, 694, 696 | ZCQ13 | 100-162 |
| 40 | 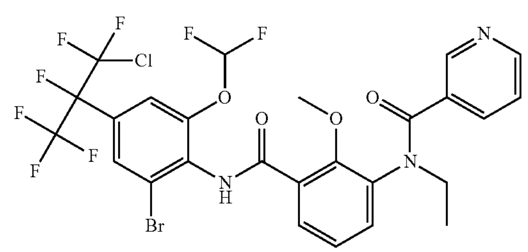 [SMILES: CCN(C(=O)c1cccnc1)c1cccc(C(=O)Nc2c(Br)cc(C(F)(C(F)(F)F)C(F)(F)Cl)cc2OC(F)F)c1OC] | 1.13 | 704, 706, 708 | ZCQ13 | 110-164 |
| 41 | 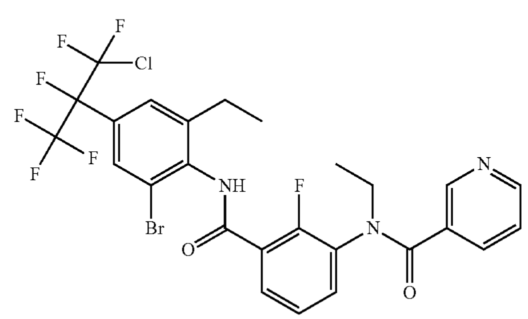 [SMILES: CCc1cc(C(F)(C(F)(F)F)C(F)(F)Cl)cc(Br)c1NC(=O)c1cccc(N(CC)C(=O)c2cccnc2)c1F] | 1.14 | 652, 654, 656 | ZDQ13 | 96-144 |

TABLE B-continued

Properties of Prepared Compounds

| Entry | STRUCTURE | RT (min) | [M + H] (measured) | Method | MP ° C. |
|---|---|---|---|---|---|
| 42 | 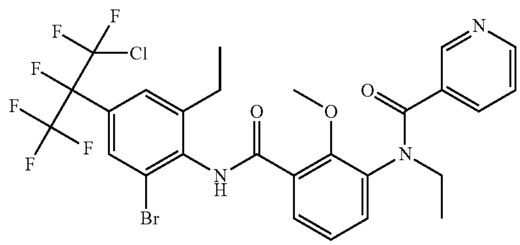 [SMILES: CCc1cc(C(F)(C(F)(F)F)C(F)(F)Cl)cc(Br)c1NC(=O)c1cccc(N(CC)C(=O)c2cccnc2)c1OC] | 1.16 | 666, 668, 670 | ZDQ13 | 80-137 |
| 43 | 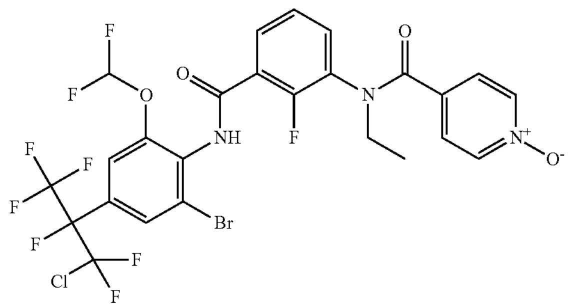 [SMILES: CCN(C(=O)c1cc[n+]([O-])cc1)c1cccc(C(=O)Nc2c(Br)cc(C(F)(C(F)(F)F)C(F)(F)Cl)cc2OC(F)F)c1F] | 1.03 | 708, 710, 712 | ZCQ13 | 115-203 |
| 44 | 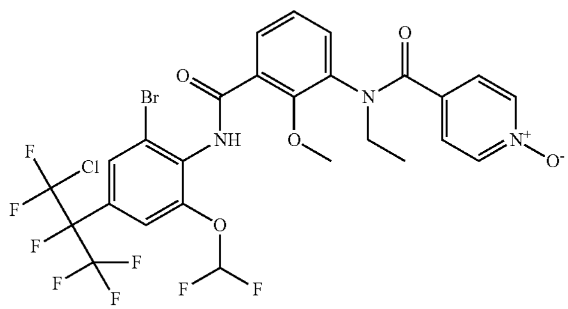 [SMILES: CCN(C(=O)c1cc[n+]([O-])cc1)c1cccc(C(=O)Nc2c(Br)cc(C(F)(C(F)(F)F)C(F)(F)Cl)cc2OC(F)F)c1OC] | 1.04 | 720, 722, 724 | ZCQ13 | 109-228 |
| 45 | 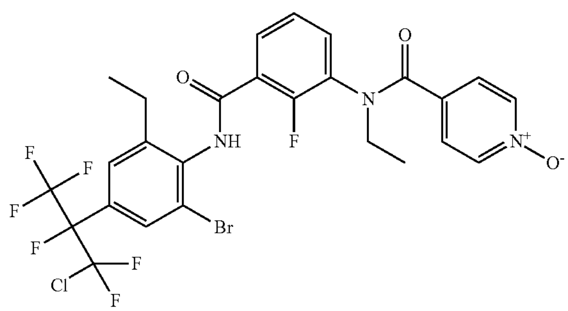 [SMILES: CCc1cc(C(F)(C(F)(F)F)C(F)(F)Cl)cc(Br)c1NC(=O)c1cccc(N(CC)C(=O)c2cc[n+]([O-])cc2)c1F] | 1.05 | 670, 672, 674 | ZCQ13 | 118-209 |
| 46 | 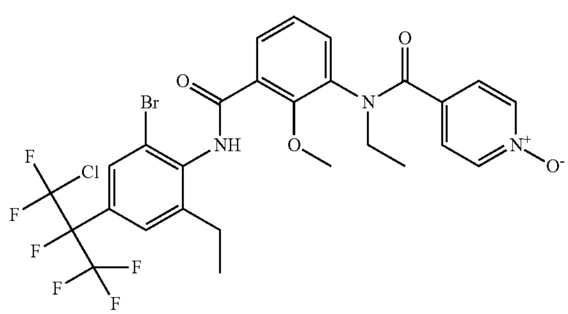 [SMILES: CCc1cc(C(F)(C(F)(F)F)C(F)(F)Cl)cc(Br)c1NC(=O)c1cccc(N(CC)C(=O)c2cc[n+]([O-])cc2)c1OC] | 1.04 + 1.06 | 682, 684, 686 | ZCQ13 | 112-220 |

TABLE B-continued

Properties of Prepared Compounds

| Entry | STRUCTURE | RT (min) | [M + H] (measured) | Method | MP ° C. |
|---|---|---|---|---|---|
| 47 | 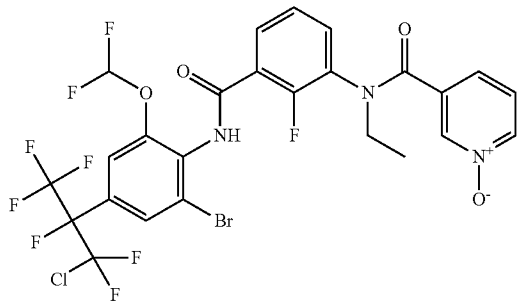 [SMILES: CCN(C(=O)c1ccc[n+]([O-])c1)c1cccc(C(=O)Nc2c(Br)cc(C(F)(C(F)(F)F)C(F)(F)Cl)cc2OC(F)F)c1F] | 1.03 | 708, 710, 712 | ZCQ13 | 98-211 |
| 48 | 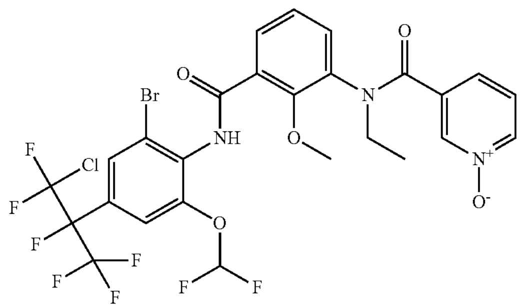 [SMILES: CCN(C(=O)c1ccc[n+]([O-])c1)c1cccc(C(=O)Nc2c(Br)cc(C(F)(C(F)(F)F)C(F)(F)Cl)cc2OC(F)F)c1OC] | 1.04 | 720, 744, 724 | ZCQ13 | 104-202 |
| 49 | 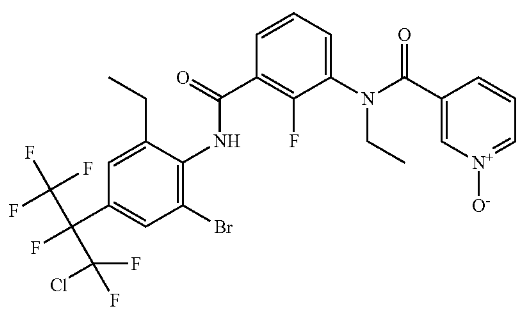 [SMILES: CCc1cc(C(F)(C(F)(F)F)C(F)(F)Cl)cc(Br)c1NC(=O)c1cccc(N(CC)C(=O)c2ccc[n+]([O-])c2)c1F] | 1.05 | 670, 672, 674 | ZCQ13 | 118-230 |
| 50 | 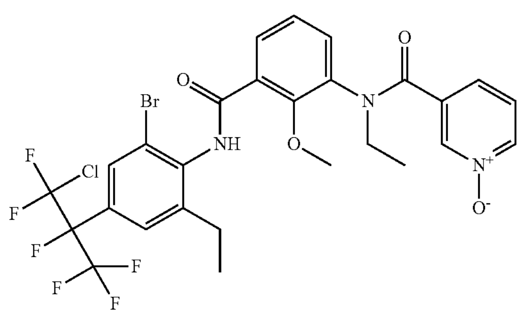 [SMILES: CCc1cc(C(F)(C(F)(F)F)C(F)(F)Cl)cc(Br)c1NC(=O)c1cccc(N(CC)C(=O)c2ccc[n+]([O-])c2)c1OC] | 1.06 | 682, 684, 686 | ZCQ13 | 99-208 |
| 51 | 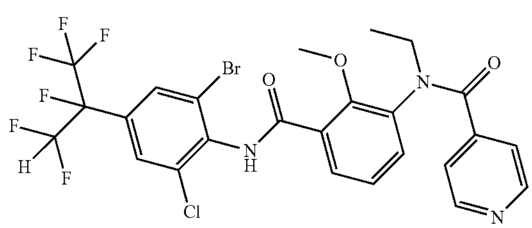 [SMILES: CCN(C(=O)c1ccncc1)c1cccc(C(=O)Nc2c(Cl)cc(C(F)(C(F)F)C(F)(F)F)cc2Br)c1OC] | 1.03 | 638, 640, 642 | OA_STANDARD | |

Biological Examples

These Examples illustrate the insecticidal and acaricidal properties of the compounds of formula (I). The tests were performed as follows:

*Bemisia tabaci* (Cotton White Fly):

Cotton leaf discs are placed on agar in a 24-well microtiter plate and sprayed with test solutions at an application rate of 200 ppm. After drying, the leaf discs are infested with adult white flies. After an incubation period of 6 DAI, samples are checked for mortality.

The following compound gave at least 80% control of *Bemisia tabaci:* 2, 3, 4, 5, 6, 7.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality The following compound gave at least 80% control of *Diabrotica balteata:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51.

*Frankliniella occidentalis* (Western Flower *Thrips*):

Sunflower leaf discs are placed on agar in a 24-well microtiter plate and sprayed with test solutions at an application rate of 200 ppm. After drying, the leaf discs are infested with a *Frankliniella* population of mixed ages. After an incubation period of 7 DAT, samples are checked for mortality.

The following compound gave at least 80% control of *Frankliniella occidentalis:* 2, 3, 4, 5, 6, 7.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for larval mortality.

The following compound gave at least 80% control of *Heliothis virescens:* 1, 2, 3, 4.

*Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality.

The following compounds gave at least 80% control of *Myzus persicae:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51.

*Myzus persicae* (Green Peach Aphid):

Roots of pea seedlings, infested with an aphid population of mixed ages, are placed directly in the test solutions at an application rate of 24 ppm. 6 days after introduction, samples are checked for mortality.

The following compounds gave at least 80% control of *Myzus persicae:* 14, 43, 44, 45, 46.

*Myzus persicae* (Green Peach Aphid):

Test compounds were applied by pipette into 24 well plates and mixed with Sucrose solution. Application rate: 12.5 ppm. The plates were closed with a stretched Parafilm. A plastic stencil with 24 holes is placed onto the plate and infested pea seedlings were placed directly on the Parafilm. The infested plate is closed with a gel blotting paper and another plastic stencil and then turned upside down. 5 days after infestation the samples were checked on mortality.

The following compounds gave at least 80% control of *Myzus persicae:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation. The following compound gave at least 80% mortality of *Plutella xylostella:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50.

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality 3 days after treatment (DAT).

The following compound gave at least 80% mortality of *Spodoptera littoralis:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51.

*Spodoptera littoralis* (Egyptian Cotton Leaf Worm):

Test compounds were applied by pipette into 24 well plates and mixed with agar. Application rate: 12.5 ppm. Lettuce seeds were placed on the agar and the multi well plate is closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples are checked for mortality 6 days after infestation.

The following compound gave at least 80% control of *Spodoptera littoralis:* 1, 2, 3, 4, 5, 6, 7, 8, 9, 10, 11, 12, 13, 14, 15, 16, 21, 23, 24, 25, 26, 31, 32, 35, 36, 39, 40, 41, 43, 44, 47, 48, 50.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs were checked for mortality.

The following compounds gave at least 80% mortality of *Tetranychus urticae:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51.

*Thrips tabaci* (Onion *Thrips*):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci:* 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51.

The invention claimed is:
1. A compound of formula (I)

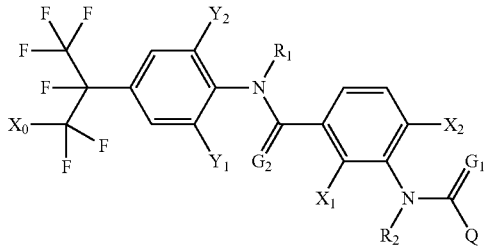 (I)

wherein
$X_0$ is bromo, chloro or hydrogen;
$X_1$ is methoxy;
$X_2$ is hydrogen;
$Y_1$ and $Y_2$ are independently chloro, bromo, iodo, $C_1$-$C_4$alkyl, $C_1$-$C_4$haloalkyl, $C_1$-$C_4$alkoxy, and $C_1$-$C_4$haloalkoxy;
$R_1$ and $R_2$ are independent of one another hydrogen, $C_1$-$C_8$alkyl, $C_2$-$C_8$alkenyl, $C_2$-$C_8$alkynyl, $C_1$-$C_8$alkylcarbonyl, $C_1$-$C_8$alkoxycarbonyl, hydroxyl, $C_1$-$C_8$-alkyloxy, and aminocarbonyl-$C_1$-$C_4$alkylene;
$G_1$ and $G_2$ are independent of each other oxygen or sulfur;
Q is a group selected from Q2, Q3, Q4 and Q5, where
Q2 is a group of formula (IIb)

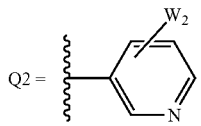 (IIb)

where $W_2$ is selected from, hydrogen, halogen, cyano, $C_1$-$C_4$ alkyl, $C_1$-$C_4$ haloalkyl, $C_1$-$C_4$ alkoxy or $C_1$-$C_4$ haloalkoxy,
Q3 is a group of formula (IIc)

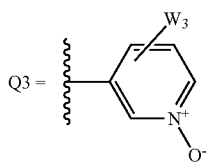 (IIc)

where $W_3$ is selected from, hydrogen, halogen, cyano, $C_1$-$C_4$ alkyl, $C_1$-$C_4$ haloalkyl, $C_1$-$C_4$ alkoxy or $C_1$-$C_4$ haloalkoxy,
Q4 is a group of formula (IId)

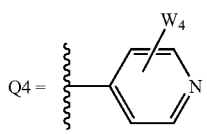 (IId)

where $W_4$ is selected, hydrogen, halogen, cyano, $C_1$-$C_4$ alkyl, $C_1$-$C_4$ haloalkyl, $C_1$-$C_4$ alkoxy or $C_1$-$C_4$ haloalkoxy,
Q5 is a group of formula (IIe)

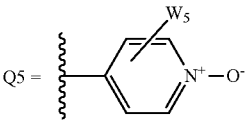 (IIe)

where $W_5$ is selected from hydrogen, halogen, cyano, $C_1$-$C_4$ alkyl, $C_1$-$C_4$ haloalkyl, $C_1$-C4 alkoxy or $C_1$-$C_4$ haloalkoxy.

2. A compound of formula (I) according to claim 1 wherein $Y_1$ and $Y_2$ are selected from Cl, Br, I, methyl, ethyl, methoxy, difluoromethoxy, and trifluoromethoxy,
$X_0$ is hydrogen or Br or Cl
$R_1$ is selected from hydrogen or $C_1$-$C_2$alkyl;
$R_2$ is selected from hydrogen, $C_1$-$C_2$alkyl;
and
$G^1$ and $G^2$ are both oxygen.

3. A compound of formula (III)

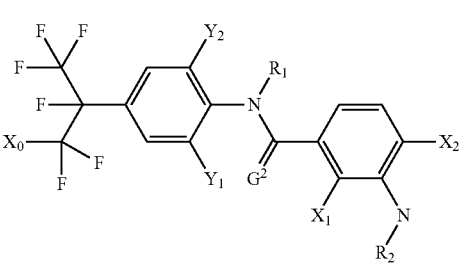 (III)

wherein $X_0$, $Y_1$, $Y_2$, $X_1$, $X_2$, $R_1$, and $R_2$ are as defined in formula (I) of claim 1.

4. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

5. An insecticidal, acaricidal, nematicidal or molluscicidal composition comprising an insecticidally, acaricidally, nematicidally or molluscicidally effective amount of a compound of formula (I) as defined in claim 1 together with an agrochemically acceptable diluent or carrier.

6. A composition according to claim 5 which further comprises one or more additional insecticidal, acaricidal, nematicidal or molluscicidal compounds.

7. A method of protecting useful plants from insects, acarines, nematodes or molluscs, comprising applying to said plants, to the locus thereof, or to plant propagation material thereof, an insecticidally, acaricidally, nematicidally or molluscicidally effective amount of a compound of formula I in claim 1.

* * * * *